(12) United States Patent
Dejardin

(10) Patent No.: US 9,072,553 B2
(45) Date of Patent: Jul. 7, 2015

(54) DEVICES AND METHODS FOR INTERLOCKING SURGICAL SCREWS AND NAILS

(71) Applicant: Loic M Dejardin, East Lansing, MI (US)

(72) Inventor: Loic M Dejardin, East Lansing, MI (US)

(73) Assignee: The Board of Trustees of Michigan State University, East Lansing, MI (US)

( * ) Notice: Subject to any disclaimer, the term of this patent is extended or adjusted under 35 U.S.C. 154(b) by 308 days.

(21) Appl. No.: 13/850,661

(22) Filed: Mar. 26, 2013

(65) Prior Publication Data

US 2014/0309637 A1 Oct. 16, 2014

Related U.S. Application Data

(62) Division of application No. 11/243,725, filed on Oct. 5, 2005, now Pat. No. 8,435,238.

(60) Provisional application No. 60/616,369, filed on Oct. 5, 2004.

(51) Int. Cl.
| | |
|---|---|
| *A61B 17/72* | (2006.01) |
| *A61B 17/17* | (2006.01) |
| *A61B 17/86* | (2006.01) |
| *A61B 17/92* | (2006.01) |
| *A61D 1/00* | (2006.01) |
| *A61F 2/30* | (2006.01) |

(52) U.S. Cl.
CPC ......... *A61B 17/7283* (2013.01); *A61B 17/1725* (2013.01); *A61B 17/72* (2013.01); *A61B 17/725* (2013.01); *A61B 17/8625* (2013.01); *A61B 17/8635* (2013.01); *A61B 17/921* (2013.01); *A61D 1/00* (2013.01); *A61F 2002/30701* (2013.01); *A61F 2002/30703* (2013.01); *A61F 2250/0081* (2013.01)

(58) Field of Classification Search
CPC ............... A61B 17/72; A61B 17/7283; A61B 17/1725; A61B 17/725; A61B 17/8635
USPC .......... 606/62–68, 70, 71, 280–299, 300–331
See application file for complete search history.

(56) References Cited

U.S. PATENT DOCUMENTS

| | | | | |
|---|---|---|---|---|
| 5,034,013 | A  * | 7/1991 | Kyle et al. ........................ | 606/62 |
| 5,122,141 | A  * | 6/1992 | Simpson et al. ................. | 606/62 |
| 5,779,704 | A  * | 7/1998 | Kim ................................. | 606/64 |
| 6,123,708 | A  * | 9/2000 | Kilpela et al. ................... | 606/62 |
| 6,296,645 | B1 * | 10/2001 | Hover et al. ..................... | 606/62 |
| 6,402,753 | B1 * | 6/2002 | Cole et al. ....................... | 606/62 |
| 6,488,684 | B2 * | 12/2002 | Bramlet et al. ................. | 606/62 |
| 6,508,820 | B2 * | 1/2003 | Bales .............................. | 606/62 |
| 7,179,260 | B2 * | 2/2007 | Gerlach et al. ................ | 606/291 |
| 7,608,075 | B2 * | 10/2009 | Tornier ............................ | 606/64 |
| 2002/0103488 | A1 * | 8/2002 | Lower et al. .................... | 606/62 |
| 2002/0111629 | A1 * | 8/2002 | Phillips ........................... | 606/62 |
| 2004/0092935 | A1 * | 5/2004 | Manderson ..................... | 606/69 |

* cited by examiner

*Primary Examiner* — Christopher Beccia
(74) *Attorney, Agent, or Firm* — Oakland Law Group PLLC

(57) ABSTRACT

The present invention demonstrates and improved interlocking nail and screw combination to repair fracture bones. The preferred combination uses an hourglass shaped intramedullary nail wherein the larger ends of the nail have holes capable of receiving screws. The holes may, or may not be conical. Further, the holes may or may not be threaded. The surgical screws have a variety of thread patterns, or lack threads. A non-threaded end is believed to improve healing because of a larger core diameter as compared to a comparably sized threaded screw end.

9 Claims, 20 Drawing Sheets

A

B

DEVICES AND METHODS FOR INTERLOCKING SURGICAL SCREWS AND NAILS

CROSS-REFERENCE TO RELATED APPLICATION

This application is a division of U.S. patent application Ser. No. 11/243,725 filed Oct. 5, 2005 which claims the benefit of U.S. Provisional Application No. 60/616,369, filed Oct. 5, 2004.

FIELD OF THE INVENTION

The present invention relates to improved intramedullary nails, improved screws to secure intramedullary nails in bones, and improved methods for stabilizing fractured bones.

BACKGROUND OF THE INVENTION

Humans, and other animals, commonly suffer from diaphyseal fractures, i.e., breaks of long bones such as the femur, tibia or humerus. Treating these fractures often requires surgery to artificially provide support normally provided by an unbroken bone.

In order to provide the needed support, metal plates are commonly placed along the exterior of a fractured bone and attached by various means, such as screws which connect with the bone cortical tissue. Unfortunately, while plates may provide good support, their implantation requires a relatively invasive surgical procedure which may be detrimental to the patient.

Other approaches include interlocking nail and screw combinations. These methods comprise placing a metal nail within the fractured bone medullary canal and locking it in place with transverse pins or screws which also connect with bone cortical tissue. This approach generally requires a shorter and less invasive surgical procedure. Unfortunately, known interlocking nail/screw combinations do not provide the same level of support as plates. In particular, interlocking nail/screw combinations are less resistant to torsional and bending forces. Clinically, this results in much slower healing times because the (at least) two portions of bone on opposite sides of the fracture are not maintained in a fixed position relative to one another, slowing tissue regeneration.

In addition, the insertion of the transverse screws or pins through the cortical tissue and the nail may be time-consuming and difficult because a surgeon cannot see the nail, or nail hole, because the nail is inside the medullary canal. Thus, it is often necessary for surgeons to rely on radiological guiding to accurately drill through cortical tissue and insert the screws or pins into the nail, exposing themselves and the patients to significant amounts of x-ray radiation during surgery.

Thus, new approaches are needed to treat long bone fractures in ways which combine relatively simple, minimally-invasive, surgical procedures with strong, stable, support means. Also, new approaches are needed to reduce or eliminate exposure to radiation during surgery.

SUMMARY OF THE INVENTION

The present invention relates to improved intramedullary nails, improved screws to secure intramedullary nails in bones, and improved methods for stabilizing fractured bones.

In one embodiment, the present invention contemplates an intramedullary nail and screw combination, comprising: a) an intramedullary nail, comprising a first end section, a central section and second end section, wherein at least one of the end sections has at least one substantially transverse conical hole therethrough, wherein the transverse conical hole has an inner surface, and wherein the diameter of the first and second end sections are larger than the diameter of the central section; and b) one or more screws each comprising a cylindrical first end section, a conical central section, and a cylindrical second end section with threads; wherein the conical central section of the screw has an outer surface configured to fit with the transverse conical hole inner surface. In one embodiment, the nail and screw combination further comprises threads on the conical central section of the screw. In one embodiment, the nail is formed of a material which has a first hardness and the screw is formed of a material which has a second hardness, and the second hardness is greater than the first hardness. In one embodiment, the threads on the conical central section of the screw are deformable. In one embodiment, the nail and screw combination further comprises threads in the transverse conical hole. In one embodiment, the threads in the transverse conical hole are deformable. In one embodiment, the nail and screw combination further comprises threads on the conical central section of the screw and threads in the transverse conical hole. In one embodiment, the threads on the conical central section of the screw are sized so as to allow interlocking with the threads in the transverse conical hole. In one embodiment, the nail and screw combination wherein, once joined, the screw conical central section outer surface and the transverse conical hole inner surface are resistant to separation when being acted upon by torsional or bending forces.

In one embodiment, the present invention contemplates a method for providing support for a fractured bone, comprising: a) providing i) a bone comprising a cortex and an inner volume within the cortex, ii) and an intramedullary nail, comprising a first end section, a central section and second end section, wherein at least one of the end sections has at least one substantially transverse conical hole therethrough, and wherein the first end section, the second end section and the central section each has a diameter, and the diameter of the first and second end sections are larger than the diameter of the central section; and iii) one or more screws each comprising a cylindrical first end section, a conical central section, and a cylindrical second end section with threads; wherein the conical central section of the screw has an outer surface and the transverse conical hole has an inner surface, and the screw conical central section outer surface is configured to contact the transverse conical hole inner surface; b) placing at least a portion of the intramedullary nail into the inner volume of the bone; and c) inserting the screw into the transverse conical hole such that the screw conical central section outer surface contacts the conical hole inner surface and the cylindrical first end section of the screw protrudes from the nail and contacts the bone cortex, the conical central section of the screw contacts the nail, and the cylindrical second end section of the screw protrudes from the nail and threads into the bone cortex. In one embodiment, inserting the screw into the transverse conical hole further comprises tightening the screw in the transverse conical hole. In one embodiment, the screw conical central section further comprises threads and the transverse conical hole further comprises threads, and wherein inserting the screw into the transverse conical hole further comprises tightening the screw in the transverse conical hole so that the screw conical central section threads and the transverse conical hole threads interlock. In one embodiment, the method is practiced during a surgical procedure on a human. In one embodiment, the method is practiced during a surgical procedure on an animal which is not human.

In one embodiment, the present invention contemplates a method for providing support for a fractured bone, comprising: a) providing a subject with a fractured bone, the fractured bone comprising a cortex and an inner volume; b) providing i) an intramedullary nail, comprising a first end section, a central section and second end section, wherein at least one of the end sections has at least one substantially transverse conical hole therethrough, and wherein the first end section, the second end section and the central section each has a diameter, and the diameter of the first and second end sections are larger than the diameters of the central section; and ii) one or more screws each comprising a cylindrical first end section, a conical central section, and a cylindrical second end section with threads; wherein the conical central section of the screw has an outer surface and the transverse conical hole has an inner surface, and the screw conical central section outer surface is configured to contact the transverse conical hole inner surface; c) placing at least a portion of the intramedullary nail into the inner volume of the bone; d) drilling one or more holes through the bone cortex in a location which is substantially in line with a transverse conical hole in the nail; and e) inserting the screw into the hole in the bone cortex and transverse conical hole such that the screw conical central section outer surface contacts the conical hole inner surface, the cylindrical first end section of the screw protrudes from the nail and contacts the bone cortex, the conical central section of the screw contacts the nail, and the cylindrical second end section of the screw protrudes from the nail and threads into the bone cortex. In one embodiment, the subject is human. In one embodiment, the subject is not human. In one embodiment, the method further comprises removing the screw and nail from the bone after the fracture heals.

In one embodiment, the present invention contemplates an intramedullary nail, comprising a first end section, a central section and second end section, wherein at least one of the end sections has one or more substantially transverse conical holes therethrough, and wherein the first end section, the second end section and the central section each has a diameter, and the diameter of the first and second end sections are larger than the diameter of the central section. In one embodiment, the intramedullary nail further comprises threads in the transverse conical hole. In one embodiment, the intramedullary nail further comprises at least a second transverse conical hole through an end section. In one embodiment, the intramedullary nail further comprises at least one transverse conical hole through each of the first and second end sections. In one embodiment, the intramedullary nail further comprises at least two transverse conical holes through each of the first and second end sections. In one embodiment, the intramedullary nail further comprises threads in the transverse conical holes. In one embodiment, at least one of the end sections is substantially cylindrical in shape. In one embodiment, the central section is substantially cylindrical in shape. In one embodiment, the diameters of the first and second end sections is substantially equal. In one embodiment, the diameters of the first and second end sections is not substantially equal.

In one embodiment the present invention contemplates a screw for securing an intramedullary nail, comprising a cylindrical first end section, a conical central section, and a cylindrical second end section with threads. In one embodiment, the screw further comprises threads on the conical central section. In one embodiment, the threads on the conical central section are deformable. In one embodiment, the threads on the conical central section have a first height, and the threads on the cylindrical second end section have a second height, and the first height is less than the second height. In one embodiment, the threads on the conical central section are separated from one another by a first distance, and the threads on the cylindrical second end section are separated from one another by a second distance, and the first distance is less than the second distance. In one embodiment, the screw further comprises an indentation in the cylindrical second end section, the indentation being of such a shape so as to accommodate a driving device, the driving device being selected from the group consisting of a flat head screw driver, a Phillips head screw driver and a hexagonal key. In one embodiment, the screw further comprises a protrusion on the cylindrical second end section, the protrusion being of such a shape so as to accommodate a driving device, the driving device being selected from the group consisting of a wrench, a ratchet/socket combination and pliers. In one embodiment, the conical central section has a relatively smaller diameter end and a relatively larger diameter end, and the relatively smaller diameter end is adjacent to the cylindrical first end section, and the relatively larger diameter end is adjacent to the cylindrical second end section. In one embodiment, the diameter of the relatively smaller diameter end of the conical central section is substantially the same as the diameter of the cylindrical first end section, and the diameter of the relatively larger diameter end of the conical central section is substantially the same as the diameter of the cylindrical second end section.

In one embodiment, the present invention contemplates an intramedullary nail and screw combination, comprising: a) an intramedullary nail, comprising a first end section, a central section and second end section, wherein each have a diameter and wherein at least one of the end sections has at least one substantially transverse conical hole therethrough, wherein the transverse conical hole has an inner surface, and wherein the diameter of the first and second end sections are larger than the diameter of the central section; and b) one or more screws each comprising a cylindrical first end section, a conical central section, and a cylindrical second end section with threads; wherein the conical central section of the screw has an outer surface configured to fit with the transverse conical hole inner surface. In one embodiment, the nail and screw combination further comprises threads on the conical central section of the screw. In one embodiment, the nail is formed of a material which has a first hardness and the screw is formed of a material which has a second hardness, and the second hardness is greater than the first hardness. In one embodiment, the threads on the conical central section of the screw are deformable. In one embodiment, the nail and screw combination further comprises threads in the transverse conical hole. In one embodiment, the threads in the transverse conical hole are deformable. In one embodiment, the nail and screw combination further comprises threads on the conical central section of the screw and threads in the transverse conical hole. In one embodiment, the threads on the conical central section of the screw are sized so as to allow interlocking with the threads in the transverse conical hole. In one embodiment, the screw conical central section outer surface and the transverse conical hole inner surface are resistant to separation when being acted upon by torsional or bending forces.

In one embodiment, the present invention contemplates a method for providing support for a fractured bone, comprising: a) providing i) a bone comprising a cortex and an inner volume within the cortex, ii) and an intramedullary nail, comprising a first end section, a central section and second end section, wherein each have a diameter and wherein at least one of the end sections has at least one substantially transverse conical hole therethrough, wherein the transverse conical hole has an inner surface, and wherein the diameter of the first and second end sections are larger than the diameter of the central section; and iii) one or more screws each comprising a cylindrical first end section, a conical central section, and a cylindrical second end section with threads; wherein the conical central section of the screw has an outer surface configured to fit with the transverse conical hole inner surface; b) placing at least a portion of the intramedullary nail into the inner volume of the bone; and c) inserting the screw into the transverse conical hole such that the cylindrical first end section of the screw protrudes from the nail and contacts the bone cortex, the conical central section of the screw contacts the nail, and the cylindrical second end section of the screw protrudes from the nail and threads into the bone cortex. In one embodiment, inserting the screw into the transverse conical hole further comprises tightening the screw in the transverse conical hole. In one embodiment, wherein the screw conical central section further comprises threads and the transverse conical hole further comprises threads, and wherein inserting the screw into the transverse conical hole further comprises tightening the screw in the transverse conical hole so that the screw conical central section threads and the transverse conical hole threads interlock. In one embodiment, the method is practiced during a surgical procedure on a human. In one embodiment, the method is practiced during a surgical procedure on an animal which is not human.

In one embodiment, the present invention contemplates a method for providing support for a fractured bone, comprising: a) providing a patient with a fractured bone, the fractured bone comprising a cortex and an inner volume; b) providing i) an intramedullary nail, comprising a first end section, a central section and second end section, wherein each have a diameter and wherein at least one of the end sections has at least one substantially transverse conical hole therethrough, wherein the transverse conical hole has an inner surface, and wherein the diameter of the first and second end sections are larger than the diameter of the central section; and ii) one or more screws each comprising a cylindrical first end section, a conical central section, and a cylindrical second end section with threads; wherein the conical central section of the screw has an outer surface configured to fit with the transverse conical hole inner surface; c) placing at least a portion of the intramedullary nail into the inner volume of the bone; d) drilling one or more holes through the bone cortex in a location which is substantially in line with a transverse conical hole in the nail; and e) inserting the screw into the hole in the bone cortex and transverse conical hole such that the cylindrical first end section of the screw protrudes from the nail and contacts the bone cortex, the conical central section of the screw contacts the nail, and the cylindrical second end section of the screw protrudes from the nail and threads into the bone cortex. In one embodiment, the patient is human. In one embodiment, the patient is not human. In one embodiment, the procedure further comprises removing the screw and nail from the bone after the fracture heals.

In one embodiment, the present invention contemplates a screw-cone-peg comprising an unthreaded cylindrical first end portion, an unthreaded conical central portion, and a threaded cylindrical second end portion. In one embodiment, the first end portion is a peg. In one embodiment, the central portion is a cone. In one embodiment, the second end portion is a screw.

In one embodiment, the present invention contemplates a screw-cone-peg in combination with an hour-glass shaped intramedullary nail. In one embodiment, the screw-cone-peg comprises an unthreaded cylindrical first end portion, an unthreaded conical central portion, and a threaded cylindrical second end portion. In one embodiment, the first end portion is a peg. In one embodiment, the central portion is a cone. In one embodiment, the second end portion is a crew.

In one embodiment, the present invention contemplates a method for providing support for a fractured bone, comprising: a) providing a patient with a fractured bone, the fractured bone comprising a cortex and an inner volume; b) providing; i) an intramedullary nail, comprising a first end section, a central section and second end section, wherein each have a diameter and wherein at least one of the end sections has at least one substantially transverse conical hole therethrough, wherein the transverse conical hole has an inner surface, and wherein the diameter of the first and second end sections are larger than the diameter of the central section; and ii) one or more screw-cone-pegs, wherein the cone of said screw-cone-peg has an outer surface configured to fit with the transverse conical hole inner surface; c) placing at least a portion of the intramedullary nail into the inner volume of the bone; d) drilling one or more holes through the bone cortex in a location which is substantially in line with a transverse conical hole in the nail; and e) inserting the screw-cone-peg into the hole in the bone cortex and transverse conical hole such that the peg of the screw-cone-peg protrudes from the nail and contacts the bone cortex, the cone of the screw-cone-peg contacts the nail, and the screw of the screw-cone-peg protrudes from the nail and threads into the bone cortex. In one embodiment, the patient is human. In one embodiment, the patient is not human. In one embodiment, the procedure further comprises removing the screw-cone-peg and nail from the bone after the fracture heals.

In one embodiment, the present invention contemplates an hour-glass shaped intramedullary nail wherein said nail comprises a population of conical holes along its length. In one embodiment, said population of conical holes are evenly spaced. In one embodiment, said conical hole contacts a conical screw. In one embodiment, said conical screw comprises a screw-cone-peg. In one embodiment, said conical hole contacts a conical plug. In one embodiment, the plug comprises polyurethane. In one embodiment, said plug comprises a threaded cylindrical second section. In one embodiment, a bone fracture pattern determines the exact screw placement, wherein said conical holes not contacted with said screws comprise plugs.

In one embodiment, the present invention contemplates a method for supporting a bone fracture comprising; a) providing; i) an hour-glass shaped intramedullary nail comprising a population of conical holes along its length, wherein said population comprises a first population portion and a second population portion; ii) a plurality of conical screws capable of insertion into said first population portion; and iii) a plurality of conical plugs capable of insertion into said second population portion; b) determining the number and location of fractures within the bone; c) inserting said plugs into said second population portion; d) inserting said nail into said bone fracture; and e) inserting said conical screws into said first population portion. In one embodiment, said conical holes are evenly spaced.

In one embodiment, the present invention contemplates a method for supporting a bone fracture comprising; a) providing; i) an hour-glass shaped intramedullary nail comprising a population of conical holes along its length, wherein said population comprises a first population portion and a second population portion; and ii) a plurality of conical screws capable of insertion into said first population portion; b) determining the number and location of fractures within the bone; c) inserting said nail into said bone fracture; and d) inserting said conical screws into said first population portion, wherein after supporting said bone fracture with said nail not all said conical holes have conical screws. In one embodiment, said conical holes are evenly spaced.

Definitions

The term "nail", as used herein, means a rod-like object which is placed inside a bone so as to support the bone after a fracture. Nails may be cylindrical, rectangular, triangular or a variety of other shapes and may have the same diameter along their entire length or may have varying diameters along their length, e.g., a nail may have large diameters at each end and a smaller diameter (i.e. it is narrower) at its center (e.g. an hourglass shape).

The term "conventional ILN", as used herein, means a traditional "interlocking nail" currently commercially available. Typically a conventional interlocking nail is compatible with the insertion of either screws or bolts to secure the conventional ILN to a bone.

The term "ILNn", as used herein, means a novel interlocking nail modified to improve resistance to torsion, compression, and angular bending when compared to conventional ILNs. For example, an ILNn may have an hourglass shape or compatible with the insertion of conical screws or conical bolts.

The term "DCP", as used herein, means a dynamic compression plate. For example a dynamic compression plate may be a broad dynamic compression plate (br-DCP). Alternatively, a dynamic compression plate may be a narrow dynamic compression plate (nw-DCP).

The term "PRC", as used herein, means a plate-rod combination device. Typically a plate-rod combination device is used in the art of bone fracture healing by the simultaneous placement of an intramedullary rod (LMR) with a bone plate (i.e., for example, a DCP).

The term "intramedullary", as used herein, means that an object is in, or may be placed in, a bone medullary canal. As used herein, an intramedullary nail may extend not only into the medullary canal (diaphysis) of a bone but also into the proximal or distal metaphysis of a bone. The term "medullary canal" may also refer to a space in the diaphysis and metaphyses.

The terms "first end section", "central section" and "second end section", as used herein, mean parts of a nail, wherein the "central section" is between the "first end section" and "second end section". Generally, a "first end section" would be the leading end of a nail when it is placed in a medullary canal, and may have a pointed or rounded tip to allow easier insertion.

The term "substantially transverse holes" as used herein, refer to any hole with a central axis that is essentially, though not necessarily exactly, perpendicular to the longitudinal axis of the object through which the hole is made.

The term "conical hole", as used herein, are holes resembling a cone in shape.

The term "cone", as used herein, refers to any surface, or portion of a surface, generated by a straight line that passing through a fixed point and moves along a fixed curve.

The term "Morse taper", as used herein, reflects the interaction of two dimensions used to describe a cone, namely its larger diameter and its taper. A taper is defined as the tangent of the angle that characterizes the cone. For example, a conical screw may have a larger diameter of 4 mm with a 0.05 taper corresponding to a cone angle of 2.8624° such that the small diameter is 3.2 mm.

The term "diameter", as used herein, means the length of a straight line through the center of an object. Object of all sizes, e.g., cylindrical, rectangular and triangular objects, have diameters. The term may be further defined as the length of the longest possible straight line through an object, from one outer edge of the object to the opposite outer edge of the object. In the case of a nail, a "diameter" of a section is measured in a direction which is essentially perpendicular to the longitudinal axis of the nail.

The term "threads" or "threaded", as used herein, means the raised helical rib going around a screw or the inside of a hole. "Threaded" screws and holes are ubiquitous and exist in numerous configurations. Threads may have various heights (depths), and may be varying distances from one another, as viewed from the side of a screw. Threads are actually not distant from one another, as they are generally a continuous bead.

The term "substantially cylindrical", as used herein, means approximately or actually having the shape of a cylinder.

The term "substantially equal", as used herein, means approximately or actually equal (e.g., within ten percent of equal).

The term "screw", as used herein, means an object which may be inserted, rotatably or otherwise, into a hole, and which may be used for "securing" or to "secure", i.e. fix or attach, one object to another. "Screws" may be, but need not be, threaded.

The terms "cylindrical first end section", "conical central section" and "cylindrical second end section", as used herein, refer to parts of a screw, wherein the "cylindrical first end section" is generally the leading edge of the screw when it is inserted into, e.g. a hole; the "cylindrical second end section" is the end distal from the "cylindrical first end section" and which may include a protrusion or indentation to aid with insertion procedure; and the "conical central section" is a section between the "cylindrical first end section" and the "cylindrical second end section". One embodiment of a "screw" as contemplated herein, is referred to as a "screw-cone-peg" (SCP). For example, an SCP cylindrical first end section may be unthreaded and referred to as a "peg". In another example, an SCP conical central section may also be unthreaded and referred to as a "cone". In another example, an SCP cylindrical second end section may be threaded and referred to as a "screw".

The term "driving device" or "driving handle device", as used herein, means any device which assists with the insertion of a screw, e.g., a flat head screw driver, a phillips head screw driver, a hexagonal (hex) key, a wrench, a ratchet/socket combination, and pliers. A driving device also includes an insertion handle, wherein the handle may optionally be coupled into an extension via a threaded portion.

The term "deformable", as used herein, means capable of having its shape altered by pressure.

The term "interlocking" or "interlock", as used herein, means to connect in such a manner that threads on a first surface interconnect or thread into threads on a second surface.

The term "bone inner volume", as used herein, means the volume enclosed by the bone cortex.

The term "substantially in line with a transverse conical hole", as used herein, in the context of drilling a hole through bone cortex, means that the central axis of the drilled hole is approximately or actually in line with the central axis of a transverse conical hole of a nail in the bone inner volume.

The term, "fits" or "configured to fit", as used herein, in the context of a screw being inserted into a nail means that the screw conical central section outer surface contacts the conical hole inner surface tightly so that there is essentially no movement between the nail and the screw.

The term, "patient", as used herein, refers to any animal (i.e., human and/or non-human) which exhibits symptoms of a fractured bone and is in need of a bone healing device (i.e., for example, ILNn, conventional ILN, DCP, IMR, or PRC). A human may be an adult human or a juvenile human. A non-human animal may include, but is not limited to, dog, cat, bird, horse, cow, sheep, goat, etc.

BRIEF DESCRIPTION OF THE FIGURES

The following figures are not intended to limit the invention disclosed herein and are presented only as examples of specific embodiments.

FIG. 9A: Traditional straight nails with a long working length $L_a$ (as measured between the two arrows). FIG. 9B; One embodiment of conical screws as contemplated herein with a short working length $L_b$ (as measured between the two arrows).

DETAILED DESCRIPTION OF THE INVENTION

Figure 1:
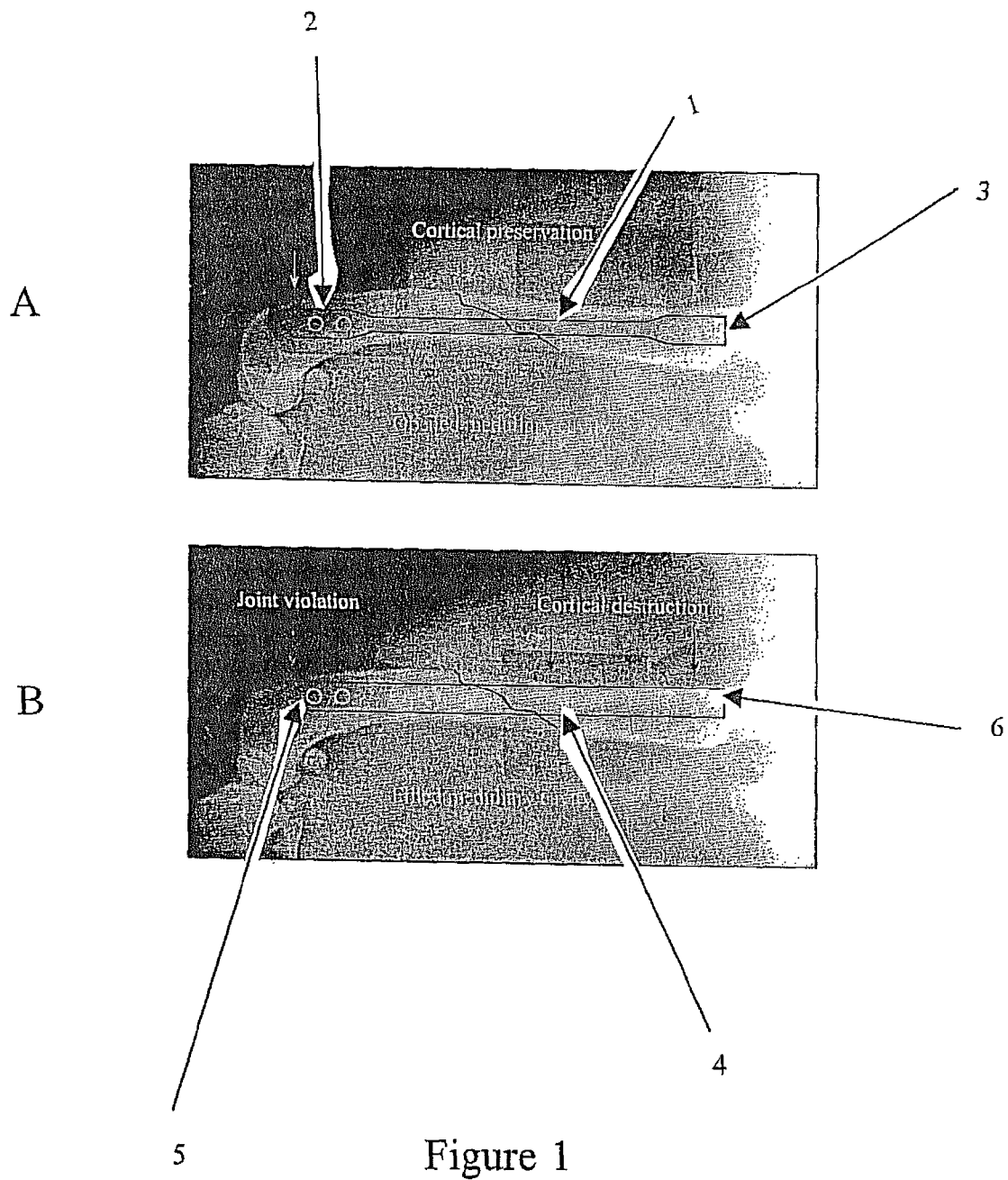
FIG. 1A shows a representative radiograph showing improved bone healing when using one embodiment of an improved fit within the medullary cavity of a femur interlocking nail (ILNn) as contemplated by the present invention. Such an ILNn configured to fit within the medullary cavity will improve bone healing.
FIG. 1B shows a representative radiograph showing poor ILN fit within the medullary cavity of a femur when using a commercially available conventional ILN. Such an ILN not configured to fit within the medullary cavity will have poor bone healing.

The present invention relates to improved intramedullary nails, improved screws to secure intramedullary nails in bones, and improved methods for stabilizing fractured bones.

Common complications of traditional intramedullary fixation devices include fracture instability, implant migration or fracture, implant rotation, and fracture shortening. Dueland et al., "Interlocking nail treatment of diaphyseal long bone fractures in dogs" *J. Am. Vet. Med. Assoc.* 214: 59-65 (1999). These complications may result in an inadvertent joint penetration when using an intramedullary fixation device that could have serious consequences. For example, an impalement and/or violation of a joint can result in a severe loss in limb function possibly due to arthritis accompanied by a loss of range of motion and, subsequently, ambulatory function.

Another routinely reported complication regarding conventional ILNs use is transcortical screw breakage. Langley-Hobbs et al., "Interlocking nail repair of a fractured femur in a turkey" *Vet. Rec.* 150: 248-249 (2002); Moses et al., "Intramedullary interlocking nail stabilization of 21 humeral fractures in 19 dogs and one cat" *Aust. Vet. J.* 80: 336-343 (2002); Duhautois, B. "Use of veterinary interlocking nails for diaphyseal fractures in dogs and cats: 121 cases" *Vet. Surg.* 32: 8-20 (2003); and Dueland et al., "Interlocking nail treatment of diaphyseal long bone fractures in dogs" *J. Am. Vet. Med. Assoc.* 214: 59-65 (1999). Mild proximal screw bending that occurs in these cases may have been due to premature weight bearing on the limb, screw size, or rotational instability. For example, all four 2 mm screws placed in a 4.7 mm conventional ILN to treat a chronic comminuted femoral fracture in a 11.4 kg domestic turkey broke by 8 weeks postoperatively. It is known that avian bone cortices, despite being thinner than mammalian cortices, support cortical bone screws. Howard, P. E. "The use of bone plates in the repair of avian fractures" *J. Am. Anim. Hos. Assoc.* 26:613-622 (1990). Broken bone screws also occur in human patients. Keating et al., "Locking intramedullary nailing with and without reaming for open fractures of the tibial shaft. A prospective, randomized study" *J Bone Jt. Surg. Am.* 79:334-41 (1997).

Although more serious complications involving conventional ILN breakage, and possible bone fracture, has occurred in some canines, it is reported that this was mainly due to technical errors such as too small a nail size or screws placed too close to the fracture. Dueland et al., "Interlocking nail treatment of diaphyseal long bone fractures in dogs" *J. Am. Vet. Med. Assoc.* 214:59-65 (1999). Currently, it is only recommended that screw positioning may provide an answer. It is recommended that screws be no closer to the fracture than 5 cm in humans. Bucholz et al., "Fatigue fracture of the interlocking nail in the treatment of fractures of the distal part of the femoral shaft" *J Bone Jt. Surg. Am.* 69:1391-1399 (1987). Further, when using 6 mm or 8 mm nails in dogs the recommended distance is 2 cm. Dueland et al., "Fatigue study of six and eight mm diameter interlocking nails with screw holes of variable size and number" *Vet. Comp. Orthop. Traumatol.* 10:194-199.

This approach, however, will most likely not be successful. In vitro studies measuring bending stiffness to failure when using ILNs found no difference in bending stiffness with four, two, or even zero screws. Dueland et al., "Structural properties of interlocking nails, canine femora, and femur interlocking nail constructs" *Vet. Surg.* 25:386-396 (1996); and Durall et al., "Interlocking nail stabilization of humeral fractures. Initial experience in seven cases" *Vet. Comp. Orthop. Traumatol.* 7:3-8 (1994).

Interlocking Nail Devices

Interlocking nails (ILNs) are increasingly used for repair of long bone fractures in dogs and cats and are considered the standard of care in humans due to their potential biological and mechanical advantages over plate fixation. Kyle et al., "Biomechanical characteristics of interlocking femoral nails in the treatment of complex femoral fractures" *Clin Orthop Relat Res* 169-173 (1991). As conventional ILN use increases, limitations are being reported and evaluated experimentally. Duhautois B. "Use of veterinary interlocking nails for diaphyseal fractures in dogs and cats: 121 cases" *Vet Surg* 32:8-20 (2003); Klein et al., "Comparison of unreamed nailing and external fixation of tibial diastases—mechanical conditions during healing and biological outcome" *J Orthop Res* 22:1072-1078 (2004); Knothe et al., "Development and testing of a new self-locking intramedullary nail system: testing of handling aspects and mechanical properties" *Injury* 31:617-626 (2000); Laflamme et al., "Proximal tibial fracture stability with intramedullary nail fixation using oblique interlocking screws" *J Orthop Trauma* 17:496-502 (2003); Lin et al., "Stress analysis of the distal locking screws for femoral interlocking nailing" *J Orthop Res* 19:57-63 (2001); Schandelmaier et al., "Biomechanical study of nine different tibia locking nails" *J Orthop Trauma* 10:37-44 (1996); Suber et al., "Two unreported modes of interlocking nail failure: breakout and screw bending" *Vet Compar Orthop Traumatol* 15:228-232 (2002); and Suber et al., "A comparison of bending and gap stiffness between interlocking nails and interlocking nails supplemented with stack pins" *Vet Compar Orthop Traumatol* 2:A12 (2002).

For example, a recent in vivo study showed that due to continuous torsional and bending instability, the use of ILNs resulted in significant reduction in healing and return to function when compared to external fixators. Klein et al., "Comparison of unreamed nailing and external fixation of tibial diastases—mechanical conditions during healing and biological outcome" *J Orthop Res.* 22:1072-1078 (2004). Similarly, an in vitro study of nine different conventional ILN designs demonstrated that consistent "play" or "slack" was present in all constructs in torsion and bending regardless of the design. Schandelmaier et al., "Biomechanical study of nine different tibia locking nails" *J Orthop Trauma* 10:37-44 (1994). Finally, a recent in vitro study showed that indeed torsional compliance with ILNs was greater than that of a plate and intramedullary rod combination (PRC), a fixation device often used in the treatment of comminuted fractures. Furthermore, the study showed that under torsional loads, conventional ILN constructs experienced up to 28° of slack, whereas PRC constructs underwent continuous deformation throughout testing. For instance, the conventional ILN construct deformation was approximately 40° while the PRC deformation was approximately 12°. von Pfeil et al., "In vitro biomechanical comparison of plate-rod combination and interlocking nail constructs in a canine tibial gap fracture model" *Am J Vet Res* 66:1469-1656 (2005). These studies suggest that current conventional ILN systems do not counteract torsional and bending forces as much as initially anticipated and consequently could result in delayed bone healing. Basinger et al., "Two techniques for supplementing interlocking nail repair of fractures of the humerus, femur, and tibia: results in 12 dogs and cats" *Vet Surg* 33:673-680 (2004).

Recent attempts at increasing nail-construct stability include such techniques as stack pinning, double ILNs, or added external fixation, which, being time-consuming and more invasive, offset the biological advantages of the conventional ILN. Lately, replacement of the locking screws with solid bolts was proposed in an attempt to further decrease construct instability. While the greater strength of bolts over comparable screws has recently been established, no study has compared the torsional and bending rigidity of conventional ILN constructs stabilized with screws or bolts.

To circumvent the shortcoming of the current conventional ILN designs, the present invention contemplates a novel interlocking nail and screw system (ILNn) that minimizes movement of the screws within the nail and increases screw-nail interface.

In addition to providing adequate stability, ILNs must be strong enough to withstand loads during the early post-operative period, particularly in comminuted fractures when cortical continuity is not achieved and/or when a sub-optimal mechanical environment (e.g. local instability) may prolong the healing time. Klein et al., "Comparison of unreamed nailing and external fixation of tibial diastases—mechanical conditions during healing and biological outcome" *J Orthop Res* 22:1072-1078 (2004). The area moment of inertia (AMI) of an implant is defined as a structural property that characterizes its ability to resist bending and is inversely proportional to the stress of a section under bending. Hibbeler R C., In: *Mechanics of materials* 4th ed. Upper Saddle River: Prentice Hall, pp. 775-788 (2000). The AMIs for several implants, including broad dynamic compression plates (br-DCP) and currently available veterinary ILNs have been determined. Since a larger AMI resulted in smaller stress levels under a given load, AMIs are used to determine the theoretical fatigue life of implants. Dueland et al., "Fatigue study of six and eight mm diameter interlocking nails with screw holes of variable size and number" *Vet Comp Orthop Traumatol* 10:194-199 (1997); and Muir et al., "Area moment of inertia for comparison of implant cross-sectional geometry and bending stiffness" *Vet Comp Orthop Traumatol* 8:146-152 (1995). AMIs may well also predict the risk of stress fractures. Milgrom et al., "The area moment of inertia of the tibia: a risk factor for stress fractures" *J Biomech* 22:1243-1248 (1989).

Fatigue failure may be induced by the application of various loading modes. For example, loading mode may include, but are not limited to, torsion (i.e., ±5 Nm or higher), bending (±3.5 Nm or higher), or compression (approximately 10-300 N). Construct biomechanical properties and/or behavior can be identified by various outcome measures including, but not limited to, compliance/stiffness, deformation of construction (i.e., angular or linear), structural damage (i.e., at bone interface or at nail interface), failure mode, or failure load. Construct failure (i.e., for example, fatigue) may be defined in various manners including, but not limited to, an $\alpha > 45°$ or structural failure of the implant and/or bone. In one embodiment, the biomechanical properties may be tested using at least three constructs including, but not limited to, nail+screw, nail+bolt, and ILNn+SCP, wherein each construct is testing under three different loading modes.

Placed along the neutral axis of the bone, ILNs have theoretical mechanical advantages similar to those of intra-medullary rods (IMR) including the ability to counteract bending stresses deleterious to bone healing. In addition, ILNs have a relatively larger area moment of inertia (AMI) than comparable bone plates, which in turn increases their bending stiffness (the AMI of a 6 nm conventional ILN is approximately 4 times that of a 3.5 mm DCP). Unlike DAR however, the conventional ILN can also resist compression and rotational forces, as a result of bone screws applied through the bone cortices and the nail, locking it to the proximal and/or distal bone fragments. Dueland et. al., "Structural properties of interlocking nails, canine femora, and femur-interlocking nail constructs" *Vet Surg* 25:386-96 (1996). A recent in vitro study using a femoral fracture model showed that conventional ILN constructs exhibited similar or greater stiffness in bending and compression as compared to constructs stabilized with a bone plate alone. Bernardé et al., "An in vitro biomechanical study of bone plate and interlocking nail in a canine diaphyseal femoral fracture model" *Vet Surg* 30:397-408 (2001). Bone plating techniques however, are more invasive, requiring extensive dissection and operative time when compared to intramedullary fixation devices.

The above studies suggest that current human or veterinary conventional ILN systems do not counteract torsional and bending forces as much as initially anticipated, which consequently could result in delayed bone healing. These instabilities also most likely play a role in the complications reported with conventional ILN use including screw bending, screw failure and nail failure. Although favorable clinical outcomes have been reported in small animals, the use of ILNs in veterinary medicine have potential limitations inherent to the simpler design of the implant itself when compared to its human counterpart. One of these limitations is the relative weakness of the nail screw holes, which may act as stress risers leading to nail failure. To reduce the risk of nail failure over time, those skilled in the art are now using smaller screws (2.7 mm instead of 3.5 mm screws in a 6 mm nail or 3.5 mm instead of 4.5 mm screws in a 8 mm nail). The corresponding reduction of nail hole diameter has been associated with a 52-fold increase in the estimated fatigue life of the nail (6 mm conventional ILN). However, the improved nail structural properties may occur to the detriment of a relatively thinner/weaker screw. In addition, the mismatch between screw and nail-hole diameters precludes rigid interaction between the screw and the nail, and as a result, rotational instability will be present following locking of screw to the bone. This undesirable phenomenon is accentuated by the progressive wear and/or flattening of the screw thread by the nail during rotational motion. Recent attempts have been made to increase construct stability with additional fixation techniques such as stack pinning, double ILNs, or external fixation. Although such techniques have shown improved construct stability, repairs are time-consuming and more invasive, thereby offsetting the biological advantages of the conventional ILN.

Considering the importance of the biological benefits of the conventional ILN fixation method, attempts have been made to determine how to overcome the shortcomings of current conventional ILN systems. A recent mathematical evaluation of ILNs determined that, along with increased nail-cortical contact, extended distance between locking screws and use of a stiffer alloy, one of the important factors contributing to increased construct stiffness and strength was increased screw-nail interface. Lin et. al., "Stress analysis of the distal locking screws for femoral interlocking nailing" *J Orthop Res* 19:57-63 (2001). Accordingly, it has been proposed that the replacement of the locking screws with similar sized bolts could decrease construct instability and strengthen the locking mechanism by providing a solid bolt-nail interface. Suber et al., "Clinical experience with the interlocking nail bolt: 27 Cases" In: *Proceedings*. 30*th Ann Conf Vet Orthop Soc* pp. 100 (2003); and Dueland et al., "Comparison of interlocking nail screws and bolts: Insertion torque, push-out strength, and mode of failure" In: *Proceedings*. 13*th Ann ACVS Vet Symp* 7 (2003). The bolts are threaded to lock on the cis-cortex of the bone, but otherwise feature a smooth core that slides into the corresponding nail hole. The above studies show that while the greater strength of bolts over screws in bending and torsion tests an evaluation of the differences in bending and torsional stability of canine conventional ILN models using screws versus bolts is apparently not available. Further, although bolts may be stronger than comparable screws, the nail remains free to slide along the bolt axis thus precluding effective locking.

To circumvent the shortcoming of current nail designs, the present invention contemplates a novel nail and screw system (ILNn) comprising improvements that increase the screw-nail interface, thereby reducing movement of the screws within the nail, and increases the nail-cortical contact surface. In one embodiment, the novel nail and screw system reduces torsional instability and improves bending stiffness.

In one embodiment, the present invention is contemplated as being useful for bone healing in both veterinary and human treatment. Axial micromotion has been shown to be beneficial to bone healing, however, torsional and bending forces are deleterious and should be counteracted by the implant fixation technique. Based on reports in the human and veterinary literature (supra), currently available ILNs may not provide sufficient post-operative stability. It has been suggested that nail construct instability likely results from an initial mismatch between screw and nail hole diameters and is accentuated by early deformation of the screw threads by the nail hole under torsional loads. von Pfeil et al., "In vitro biomechanical comparison of plate-rod combination and interlocking nail constructs in a canine tibial gap fracture model" *Am J Vet Res* 66:1469-1656 (2005).

Figure 15:
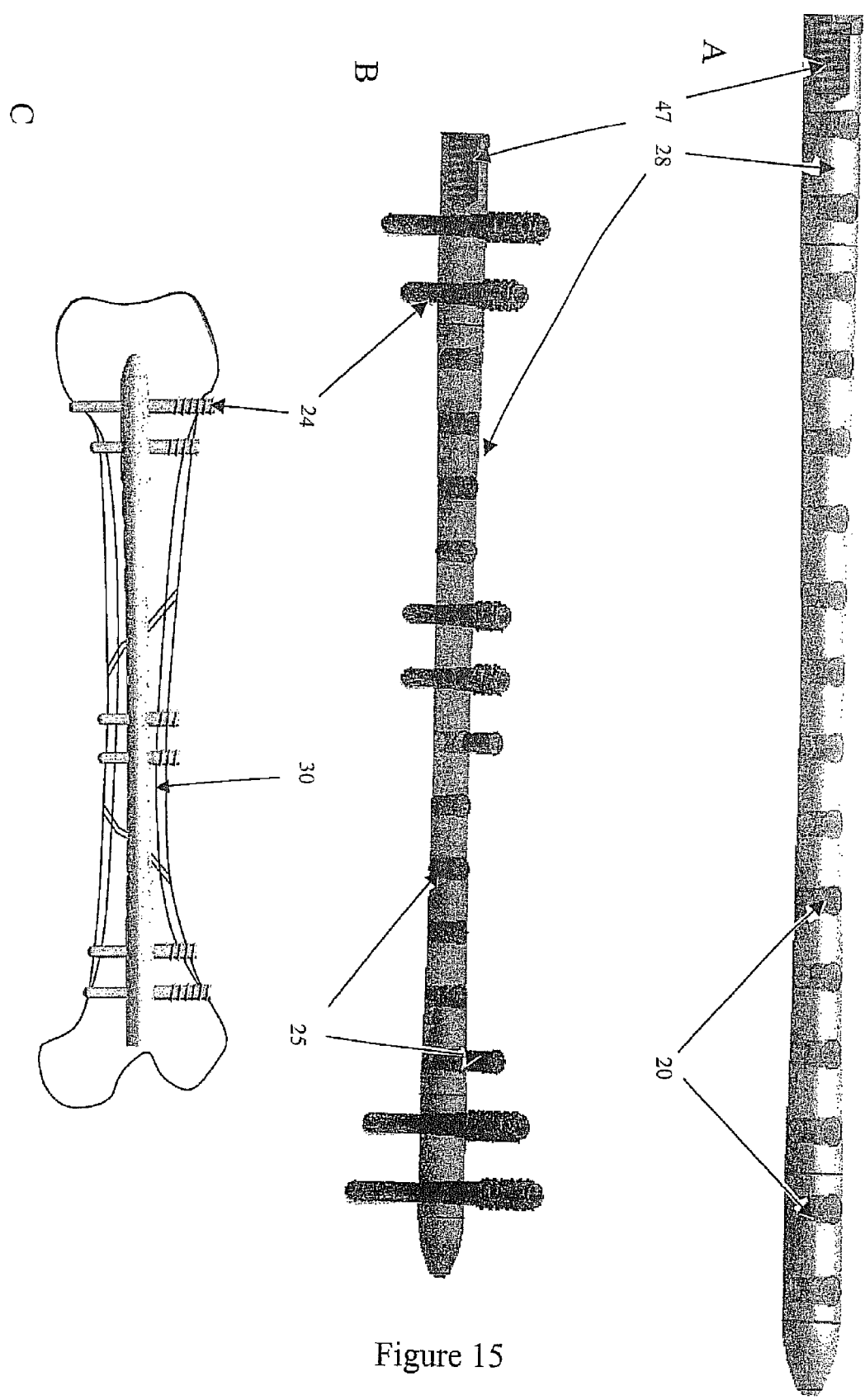
FIG. 15 shows one embodiment of an ILNn 28 wherein conical holes are evenly spaced along its length. Panel A illustrates a plan view of the ILNn. Panel B demonstrates that the ILNn holes may be optionally inserted with a conical screw (i.e., for example, an SCP 24) or a conical plug 25 (i.e., for example, polyurethane). Panel C illustrates how the ILNn may be inserted into a fractured bone 30.

In one embodiment, the present invention contemplates an hour-glass shaped intramedullary nail wherein said nail comprises a population of conical holes. In one embodiment, the population is evenly spaced along its length. In FIG. 15 a representative ILNn 28 is presented having a threaded extension coupling 47 along its length a plurality of conical holes 20 (Panel A), that may have inserted a plug 25 or a conical screw 24 (i.e., for example, an SCP). FIG. 15B. The ILNn may then be inserted into the medullary cavity of a fractured bone 30 locked in place using conical screws 24. FIG. 15C. One advantage of an ILNn with an evenly spaced population of conical holes resides in more efficient and cost-effective manufacturing. For example, it is anticipated that any ILNn of a specific length and shape may be useful for a multitude of fracture types. After evaluating a fractured bone pattern, medical personnel can then determine which conical holes do not require screw placement. These are then either plugged, or remain empty, before surgical insertion of the ILNn into the medullary space. In one embodiment, said population of conical holes are evenly spaced. In one embodiment, said conical hole contacts a conical screw. In one embodiment, said conical screw comprises a screw-cone-peg. In one embodiment, said conical hole contacts a conical plug. In one embodiment, said plug comprises a polyurethane. In one embodiment, the plug comprises a threaded cylindrical second section. In one embodiment, a bone fracture pattern determines the exact screw placement, wherein said conical holes not contacted with said screws comprise plugs.

In one embodiment, the present invention contemplates a method for supporting a bone fracture comprising; a) providing; i) an hour-glass shaped intramedullary nail comprising a population of conical holes along its length, wherein said population comprises a first population portion and a second population portion; ii) a plurality of conical screws capable of insertion into said first population portion; and iii) a plurality of conical plugs capable of insertion into said second population portion; b) determining the number and location of fractures within the bone; c) inserting said plugs into said second population portion; d) inserting said nail into said bone fracture; and e) inserting said conical screws into said first population portion. In one embodiment, said conical holes are evenly spaced.

In one embodiment, the present invention contemplates a method for supporting a fractured bone comprising; a) providing; i) an hour-glass shaped intramedullary nail comprising a population of conical holes along its length, wherein said population comprises a first population portion and a second population portion; and ii) a plurality of conical screws capable of insertion into said first population portion; b) determining the number and location of fractures within the bone; c) inserting said nail into said fractured bone; and e) inserting said conical screws into said first population portion, wherein after supporting said bone fracture with said nail not all said conical holes have conical screws. In one embodiment, said conical holes are evenly spaced. In one embodiment, the method further comprises identifying said first population portion for said screw insertion.

To circumvent the mechanical shortcoming of current nail designs, while preserving the biological benefit of using smaller unreamed nails, an ILNn system has been developed that: i) significantly reduces relative motion between the locking device and the nail thereby locking the construct; ii) increases the nail-bone contact area at the metaphyseal level while limiting contact between the nail and endocortices throughout the diaphyseal medullary cavity; iii) has theoretical bending strength similar to that of existing ILNs based on area moment of inertia calculations; and iv) will eliminate torsional instability when compared to a traditional conventional ILN of similar size.

Hourglass Interlocking Nails

In one embodiment, the present invention contemplates an hour-glass shaped interlocking nail having improved strength over a standard bone plate configuration.

The fixation method considered to be the standard of care for repair of comminuted diaphyseal fractures in mid-sized dogs (20-30 kg) is the bone plate. Peirmattei et al., In: *Piermattei and Flo's handbook of small animal orthopedics and fracture repair* 3rd ed. W.B. Saunders Company, Philadelphia. pg 125 (1997). While the 3.5 mm narrow and 3.5 mm broad dynamic compression bone plate (br-DCP) have been the most commonly used plates in veterinary medicine, the 3.5 mm narrow dynamic compression bone plate (nw-DCP) provides the ideal strength of fixation for mid-size dogs.

In the late 1980's and early 1990's a new concept of biological internal fixation was evolving. Plate-induced osteoporosis was a recognized complication in both humans and animals and was thought to be the result of interruption of cortical blood flow and stress-shielding following internal fixation. In order to provide a more biologically advantageous plate fixation method, the limited contact dynamic compression plate (LC-DCP) was developed to replace the br-DCP. The LC-DCP has a trapezoidal shape in cross-section, with undercuts that form arcs that interrupt the contact surface. Little et al., "Bending properties of stainless steel dynamic compression plates and limited contact dynamic compression plates" *Vet Comp Orthop Traumatol.*, 14(2):64-68 (2001); and. Perren et al. "The limited contact dynamic compression plate (LC-DCP)" *Arch Orthop Trauma Surg.* 109(6):304-10 (1990).

As a result, the LC-DCP minimizes vascular damage to the plated bone segment compared to the br-DCP, resulting in improved healing. In addition to biological advantages, the LC-DCP has a more uniform bending stiffness throughout the length of the plate, regardless of the presence of screw holes. However, it has been shown that the LC-DCP is weaker in strength and stiffness when compared in vitro to a similar sized br-DCP. This means that while the LC-DCP is an improvement on the biological side of fracture fixation, it is not comparable to a br-DCP in terms of fixation strength.

In order to address the above limitations of bone plating alone, the combination of a bone plate with an intra-medullary rod (IMR) has been recommended. Hulse et al. "Reduction in plate strain by addition of an intramedullary pin" *Vet Surg* 26:451-459 (1997). In an in vitro study, Hulse et al. demonstrated that a plate-rod combination (PRC) consisting of a 3.5 mm DCP and an IMR filling 50% of the medullary cavity, achieved a two-fold reduction in plate stress relative to plate alone, and an estimated 10-fold increase in plate fatigue life. This surgery is challenging due to the difficulty of screw placement around the IMR. In addition, if not carefully applied, PRCs may induce concomitant lesions of the intra- and extra-osseous blood supply.

In one embodiment, an improved interlocking nail contemplated by the present invention comprises biological fracture fixation with a minimally invasive surgery while preserving the mechanical environment necessary for optimal bone healing. In one embodiment, a minimal soft tissue dissection and minimal implant interference is performed as compared to plates. In one embodiment, an improved interlocking nail is selected from the group comprising 4 mm, 4.7 mm, 6 mm and 8 mm widths. In one embodiment, a 6 mm nail provides a biologically advantageous fixation and interrupts less cortical blood flow than an 8 mm nail. An 8 mm conventional ILN construct can have greater stiffness than a 3.5 mm broad DCP construct in bending and compression. Bernardé et al., "An in vitro biomechanical study of bone plate and interlocking nail in a canine diaphyseal femoral fracture model" *Vet Surg* 30:397-408 (2001).

Since the 3.5 mm narrow DCP provides adequate strength of fixation, 8 mm conventional ILN implants actually provide much more stiffness and strength than is required for repair of fractures in this patient group. Although no studies have been done comparing the 6 mm conventional ILN to the PRC, since the area moment of inertia (AMI) of a 6 mm conventional ILN is greater then that of both the 3.5 mm narrow and broad DCP it can be inferred that the 6 mm conventional ILN provides adequate strength and stiffness for these fractures (Table 1).

TABLE 1

Comparison of area moment of inertial for several conventional ILN implants.

| Conventional Implants (solid sections) | I (mm$^4$) |
|---|---|
| 3.5 narrow DCP | 22.5 |
| 3.5 broad DCP | 54.9 |
| 6 mm ILN | 63.6 |
| 8 mm ILN | 201.0 |

Table 1 compares the area moment of inertia (I) for AO/ASIF bone plates and between several conventional ILN implants (calculated based on $I=(\pi * R^4)/4$). Muir et al., "Area moment of inertia for comparison of implant cross-sectional geometry and bending stiffness" *Vet Comp Orthop Traumatol* 8:146-152 (1995). A greater AMI is associated with greater stiffness and greater strength. This data highlights the fact that a 6 mm conventional ILN has comparable strength and stiffness to the commonly used 3.5 mm broad DCP as well as the fact that the strength of an 8 mm nail may be excessive. Excessive implant strength may in turn shield the bone from physiological stresses vital to bone healing and remodeling following fracture. Because this phenomenon, known as "stress shielding" or "stress protection", jeopardizes bone healing and may lead to osteopenia, the use of implants which are too large or too strong is not recommended.

Although it is not necessary to understand the mechanism of an invention, it is believed that a 6 mm improved interlocking nail provides similar strength and stiffness to currently available larger nail and does not impair the intramedullary blood supply. However, currently commercially available 6 mm conventional ILN require the use of 2.7 mm screws, which are small and increase the occurrence of screw/implant failure. For that reason alone, the 8 mm conventional ILN is being used in mid-sized dogs because such implant can handle the stronger 3.5 mm screws thus reducing the risk of implant failure.

Clearly, the current state of the art prefers an 8 mm nail in order to provide large enough screws to reduce the risk of implant failure. The present invention contemplates a 6 mm nail providing adequate strength and stiffness while being the optimal for maintaining blood supply. In one embodiment, an interlocking nail comprising a 6 mm tapered end for contacting the bone shaft also comprises an 8 mm end for screw insertion. In one embodiment, the tapered nail is used in long bones, which feature larger extremities (the metaphyses) capable of accepting the larger nail ends. In one embodiment, a narrower central portion of the interlocking nail allows optimal placement within the curved diaphysis of long bones (i.e., for example, presenting an hourglass shape). In order to place a large conventional ILN, the surgeon has to ream the medullary cavity. As a result of the curved shape of long bones, this will remove bone material vital in maintaining the integrity of the construct. In other words, bone reaming jeopardizes the bone/nail interface, particularly at the tips of the nail, and is likely to result in either secondary iatrogenic fractures or even penetration of adjacent joint spaces.

Contrary to ILNs used in humans, which are routinely implanted following reaming of the medullary cavity, veterinary ILNs are generally used without preliminary reaming. Reaming allows for implantation of larger, potentially stronger nails and results in a more extensive and intimate contact between nail and endocortices, thereby improving repair stability. Mayr E., "Tibial fractures" *Chirurg* 73:642-661 (2002). The procedure, however, severely impairs the medullary blood supply and has been associated with a higher incidence of infection and fat embolism. Heim et al., "Intramedullary pressure in reamed and unreamed nailing of the femur and tibia—an in vitro study in intact, human bones" *Injury* 24 Suppl 3:S56-63 (1993); Krettek C., "Principles of intramedullary fracture stabilization" *Unfallchirurg* 104:639-651 (2001); and Klein et al., "Reaming versus non-reaming in medullary nailing: interference with cortical circulation of the canine tibia" *Arch Orthop Trauma Surg* 109: 314-316 (1990). The use of unreamed ILNs, in contrast, is reported to have potential biological advantages, such as preservation of the endosteal and medullary blood supply. Krettek C. "Principles of intramedullary fracture stabilization" *Unfallchirurg* 104:639-651 (2001); Klein et al., "Reaming versus non-reaming in medullary nailing: interference with cortical circulation of the canine tibia" *Arch Orthop Trauma Surg* 109:314-316 (1990); Krettek et al., 'New developments in stabilization of dia- and metaphyseal fractures of long tubular bones" *Orthopade* 26:408-421 (1997); Runkel et al., "Bone remodeling after reamed and unreamed intramedullary nailing. A histomorphometric study" *Unfallchirurg* 97:385-390 (1994); and Schandelmaier et al., "Advantages of the unreamed tibial nail in comparison with external fixator in treatment of grade 3 B open tibial shaft fractures" *Unfallchirurg* 100:286-293 (1997). It may, however, place the construct at a mechanical disadvantage by reducing the bone/nail interface contact area. Mayr E. "Tibial fractures" *Chirurg* 73:642-661 (2002). This suggests that, while from a biological stand point, the use of unreamed nails may be preferable, from a mechanical standpoint, post-operative construct stability of unreamed ILNs relies primarily on the integrity and efficacy of the locking mechanism. Duda et al., "Mechanical boundary conditions of fracture healing: borderline indications in the treatment of unreamed tibial nailing" *J Biomech* 34:639-650 (2001). In one embodiment, the present invention contemplates an hourglass shaped nail that will accommodate natural bone curvatures without the need for increasing the diameter of the medullary cavity via reaming.

Although it is not necessary to understand the mechanism of an invention, it is believed that this hourglass shape provides the optimum conformation for use in long bones and represents an ideal compromise with respect to the preservation of a balanced biological and mechanical environment necessary for improved healing.

FIG. 1A illustrates an hour-glass shaped ILNn that is configured to fit within a medullary cavity using a representative radiograph. Although it is not necessary to understand the mechanism of an invention, it is believed that such a configuration improves healing due to a decreased reduction in neovascularization when compared to a conventional ILN. The figure shows one embodiment of an intramedullary nail of the present invention having a narrow medullary portion 1 flanked by wider proximal end 2 distal end 3, wherein both proximal end 2 and distal end 3 each comprise two screws as contemplated herein (although embodiments with additional screws are contemplated). Although it is not necessary to understand the mechanism of an invention, it is believed that the narrow medullary portion results in less bone marrow injury thus resulting in healthier bone marrow (i.e., cortical preservation) and improved bone healing. The improved healing may be seen as reflected by an opened medullary cavity.

In contrast, FIG. 1B illustrates a conventional ILN that is not configured to fit within a medullary cavity using a representative radiograph. This convention ILN design results in poor healing due to decreased neovascularization. The figure shows an intramedullary nail having a medullary portion 4 flanked by a proximal end 5 and distal end 6 wherein all have the same width. The healing results are consistent with the medullary portion 4 damaging the bone marrow (i.e., cortical destruction) thus resulting in poor healing. The poor healing may be seen as reflected by a filled medullary cavity.

Large nails warrant a strong locking system (large screws), even to the potential detriment of the diaphyseal integrity and possible stress shielding of the bone, the new nail represents an optimal alternative with regard to both the biological and mechanical environment required for bone healing.

Currently available conventional ILNs demonstrate intra- or post-operative instability when used for small animal bone repair. Duhautois B., "Use of veterinary interlocking nails for diaphyseal fractures in dogs and cats: 121 cases" *Vet Surg* 32:8-20 (2003); Basinger et al., "Two techniques for supplementing interlocking nail repair of fractures of the humerus, femur, and tibia: results in 12 dogs and cats" *Vet Surg* 33:673-680 (2004); and Dueland et al., "Interlocking nail treatment of diaphyseal long-bone fractures in dogs" *J Am Vet Med Assoc* 214:59-66 (1999). In these studies, 12% to 14% of the cases showed delayed healing, or required supplementation of the initial conventional ILN repair to provide adequate stability. Delayed union rates, as high as 18%, have also been reported with the use of unreamed tibial nails in people. Goldhahn et al., "Treatment methods and outcomes of tibial shaft fractures in Switzerland. A prospective multicenter study of the Swiss AO" *Swiss Surg* 6:315-322 (2000). Further, several in vivo experimental studies using tibial gap fracture models have reported the deleterious effect of torsional and shear motion on early bone healing. Goodship et al., "The influence of induced micromovement upon the healing of experimental tibial fractures" *J Bone Joint Surg Br* 67:650-655 (1985); Lewallen et al., "Comparison of the effects of compression plates and external fixators on early bone-healing" *J Bone Joint Surg Am* 66:1084-1091 (1984); Wu et al., "Comparison of osteotomy healing under external fixation devices with different stiffness characteristics" *J Bone Joint Surg Am* 66:1258-1264 (1984); Augat et al., "Shear movement at the fracture site delays healing in a diaphyseal fracture model" *J Orthop Res* 2003; 21:1011-1017 (2003); Duda et al., "Interfragmentary movements in the early phase of healing in distraction and correction osteotomies stabilized with ring fixators" *Langenbeeks Arch Surg* 387:433-440 (2003); and Klein et al., "The initial phase of fracture healing is specifically sensitive to mechanical conditions" *J Orthop Res* 21:662-669 (2003).

Studies such as those above, supported by experimental evidence of construct instability with current human and veterinary nails, emphasize an unfulfilled need in the art for a more effective conventional ILN design. Schandelmaier et al., "Biomechanical study of nine different tibia locking nails" *J Orthop Trauma* 10:37-44 (1996); and von Pfeil et al., "In vitro biomechanical comparison of plate-rod combination and interlocking nail constructs in a canine tibial gap fracture model" *Am J Vet Res* 66:1469-1656 (2005). In one embodiment, the present invention contemplates an ILNn system having significantly improved the torsional stability as compared to currently available 8 mm ILNs. Although it is not necessary to understand the mechanism of an invention, it is believed that this torsional stability improvement is based upon the absence of slack.

Figure 16:
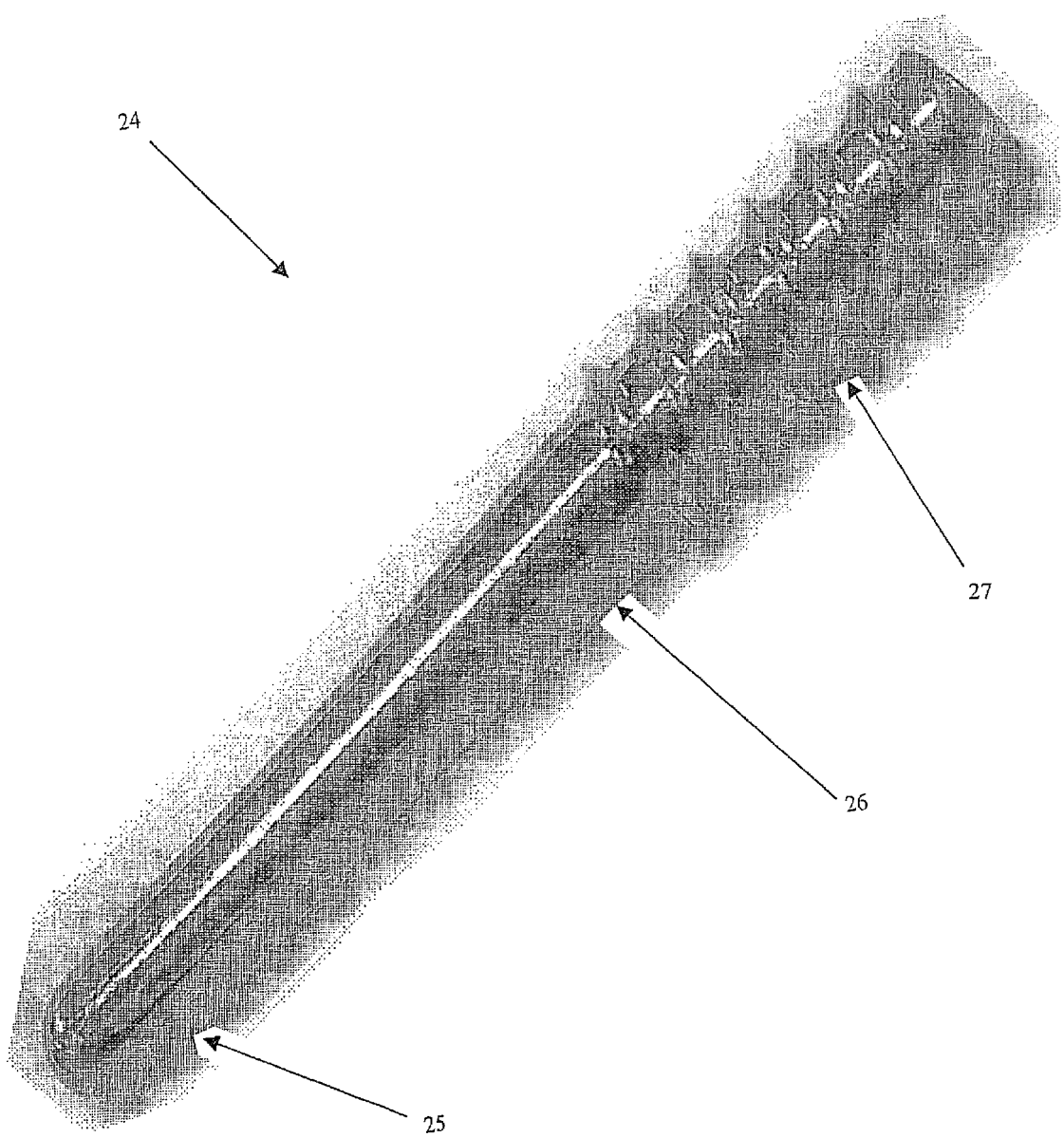
FIG. 16 shows one embodiment of a conical screw comprising a screw-cone-peg (SCP) 24.
Figure 17:
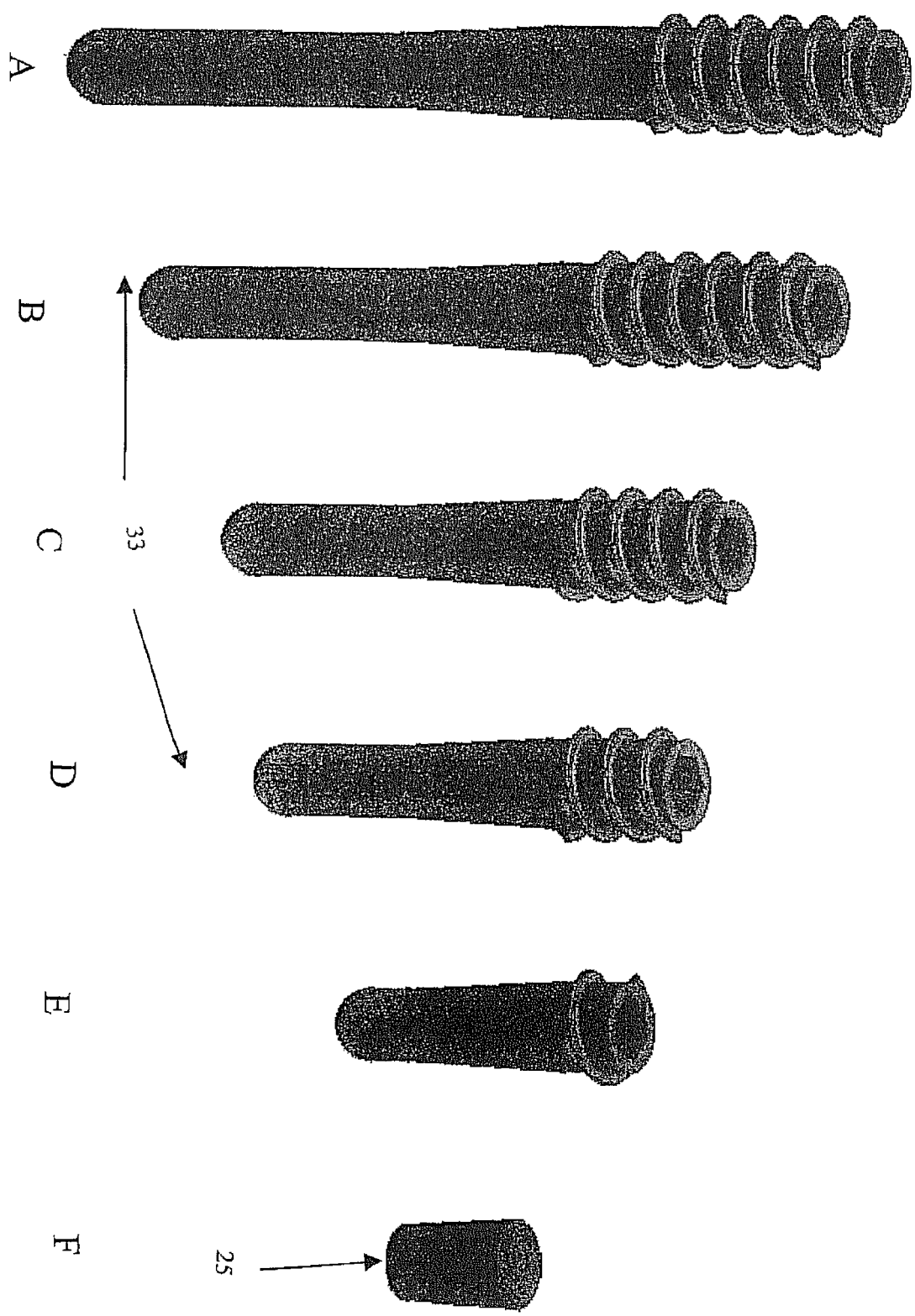
FIG. 17 shows five different embodiments of a conical screw 33 (A-E) and a plug 25 (F). Note that the conical screw may be of different lengths and thread patterns (i.e., 6 full threads-1 full thread).

In one embodiment, a conical screw, such as a screw-cone-peg (SCP) 24, comprises a Morse taper between the cone 26 and peg 25, thereby eliminating motion at the interface between the nail and the locking device. See FIG. 16. Although it is not necessary to understand the mechanism of an invention, it is believed that Morse tapers increase the effective interlocking between an ILNn and a conical screw. For example, a Morse taper may be exemplified by that of a first cone within a second cone. In one embodiment, the present embodiment contemplates a first cone comprising a conical screw and a second cone comprising a conical hole. In one embodiment, the conical screw and conical hole are both uniformly tapered. When the conical screw is inserted into the conical hole they come into intimate contact. Although it is not necessary to understand the mechanism of an invention, it is believed that the conical screw compresses the walls of the conical hole as it is inserted. Thus, the accumulated stresses inside the screw and hole wall keep both components fixed together. One recent study of threaded bolts locking into threaded holes demonstrated faster healing and recovery in bone fractures. Kaspar et al., "Angle Stable Locking Reduces Interfragmentary Movements And Promotes Healing After Unreamed Nailing. Study Of A Displaced Osteotomy Model In Sheep Tibiae" *J Bone Joint Surg* 87:2028-2037 (2005).

An SCP cylindrical first end may be unthreaded and referred to as a "peg" 25. In another example, an SCP conical central section may also be unthreaded and referred to as a "cone" 26. In another example, an SCP cylindrical second end section may be threaded and referred to as a "screw" 27. Although it is not necessary to understand the mechanism of an invention, it is believed that the Morse taper design facilitates the insertion of the SCP by providing a self-centering feature even in the presence of slight misalignment between cortical pilot hole and nail hole. It is further believed that this taper may help reduce the incidence of missed holes in clinical cases. A smooth taper has several potential advantages including, but not limited to, a low manufacturing cost and low susceptibility to iatrogenic damage during drilling.

The strength and failure pattern of ILNs depends on the design and size of the nail hole and locking device. Lin et al., "Stress analysis of the distal locking screws for femoral interlocking nailing" *J Orthop Res* 19:57-63 (2001); Gaebler et al., "Fatigue strength of locking screws and prototypes used in small-diameter tibial nails: a biomechanical study" *J*

*Trauma* 47:379-384 (1999); and Gaebler et al., "The fatigue strength of small diameter tibial nails" *Injury* 32:401-405 (2001). For example, in comminuted fractures, implants are mainly subjected to bending stresses. Muir et al., "Area moment of inertia for comparison of implant cross-sectional geometry and bending stiffness" *Vet Compar Orthop Traumatol* 8:146-152 (1995). Consequently, the ILNn's contemplated herein were designed to accommodate AMIs calculated using theoretical bending conditions.

Although it is not necessary to understand the mechanism of an invention, it is believed that the AMI of an implant is a structural property that characterizes the geometrical distribution of the material with respect to the axis of loading. All things being equal, an implant with a larger AMI will sustain lower stresses during cyclic loading, which in turn will extend its fatigue life. Dueland et al., "Fatigue study of six and eight mm diameter interlocking nails with screw holes of variable size and number" *Vet Comp Orthop Traumatol* 10:194-199 (1997). One limitation of early veterinary conventional ILN designs was the weakness of the nail holes, which acted as stress risers leading to nail failure. Dueland et al., "Interlocking nail treatment of diaphyseal long-bone fractures in dogs" *J Am Vet Med Assoc* 214:59-66 (1999). Based on AMI, ILNs are believed weakest at the nail hole under mediolateral bending conditions. It is known that by reducing the screw hole diameter from 4.5 mm to 3.5 mm results in a 5.7-fold increase in local AMI and translates into an 8-fold increase in the nail fatigue life. Dueland et al., "Fatigue study of six and eight mm diameter interlocking nails with screw holes of variable size and number" *Vet Comp Orthop Traumatol* 10:194-199 (1997). Although this design change improves the nail structural properties it detrimentally results in a thinner and weaker screw (i.e., for example, ~3-fold decrease in screw AMI).

In one embodiment, the present invention solves this problem by an ILNn having a locking device AMI equal to or greater than that of the 4.5 mm screw and a nail AMI, at the level of the holes, similar to that of the 8 mm nail with 3.5 mm screws. Although the corresponding AMI of an ILNn is slightly smaller than that of the ILN8-3.5 mm screw (i.e., 62.1 mm$^4$ and 65.6 mm$^4$, respectively), it is 64% greater than that of an ILN8-4.5 mm screw. Consequently, it is believed that an ILNn has an estimated fatigue life similar to that of the currently available ILN8 with 3.5 mm screws. Furthermore, the absence of slack and improved stability of the ILNn results in shorter healing time, thereby balancing out any potential slight theoretical decreases in ILNn fatigue life.

In some embodiments, an ILNn hourglass design provides several potential benefits and advantages over ILNs already known in the art. First, an ILNn contributes to preserving the endosteum and improves restoration of the medullary blood supply following implantation, thereby enhancing the bone healing rate. Krettek C., "Principles of intramedullary fracture stabilization" *Unfallchirurg* 104:639-651 (2001); Klein et al., "Reaming versus non-reaming in medullary nailing: interference with cortical circulation of the canine tibia" *Arch Orthop Trauma Surg* 109:314-316 (1990); and Runkel et al., "Bone remodeling after reamed and unreamed intramedullary nailing. A histomorphometric study" *Unfallchirurg* 97:385-390 (1994). In one embodiment, the hourglass design facilitates ILNn implantation into curvilinear bones by limiting contact between the nail and the endocortices.

One study suggests that an 8 mm nail may have a ten-fold increase in fatigue life when compared to a 6 mm nail. Dueland et al., "Fatigue study of six and eight mm diameter interlocking nails with screw holes of variable size and number" *Vet Comp Orthop Traumatol* 10:194-199 (1997). Further, a 3.5 mm br-DCP is reported to have a comparable fatigue life as an 8 mm nail. Large 8 mm nails may not be preferable since the AMI of a 6 mm nail solid section is similar to that of a 3.5 mm br-DCP (i.e., ~64 mm$^4$ vs. ~55 mm$^4$, respectively). Consequently, the strength of an 8 mm nail, with an AMI of 201 mm$^4$ (solid section), is unwarranted. Furthermore, large medullary implants (i.e., for example, 8 mm nails) have been shown to significantly impede the cortical blood supply. Klein et al., "Comparison of unreamed nailing and external fixation of tibial diastases—mechanical conditions during healing and biological outcome" *J Orthop Res* 22:1072-1078 (2004).

Another potential benefit of an hourglass shaped ILNn is an improved AMI consistency over the various sections of the ILNn (i.e., 62.1 mm$^4$ at the nail hole versus 63.62 mm$^4$ within the central region). Although it is not necessary to understand the mechanism of an invention, it is believed that a consistent ILNn AMI as compared to the ILN8 (i.e., 65.6 mm$^4$ at the nail hole versus 201.06 mm$^4$ within the central region) results in more uniform structural properties along the nail. It is further believed that this improved consistency reduces the deleterious effects of stress risers and the risk of implant fatigue failure. Perren S M, "The concept of biological plating using the limited contact-dynamic compression plate (LC-DCP). Scientific background, design and application" *Injury* 22 Suppl 1:1-41 (1991).

Another advantage of an ILNn resides in the fact that, in one embodiment, a bullet-shaped first cylindrical section facilitates reduction of the fracture, particularly with regard to length restoration, without increasing the risk of penetration of the distal joint associated with the use of trocar points. The oblong tip of this ILNn embodiment, as compared to some flat truncated tips in currently available ILNs, facilitates insertion through the proximal metaphysis and permits deep anchorage into the distal metaphysis, which in turn may allow for treatment of a wider variety of fractures.

The development of biomechanical bone implants has been hampered by large standard deviations due to variations in the shape and material properties of bones. This is true for both humans and animals. Szivek J A., "Synthetic materials and structures used as models for bone" In: *Mechanical testing of bone and the bone-implant interface*. An Y H & Drauhgn R A, eds., Boca Raton: CRC Press LLC, pp. 159-171 (2000). In order to solve this problem a canine tibia model was developed which limits inter-specimen variability thereby allowing for a better evaluation of the implant. Further, even simple tube models of various materials do not mimic the complex shapes predicted by physiological load models when fracture fixation devices are evaluated. Szivek J A., "Synthetic materials and structures used as models for bone" In: *Mechanical testing of bone and the bone-implant interface*. An Y H & Drauhgn R A, eds. Boca Raton: CRC Press LLC, pp. 159-171 (2000); Aper et al., "Effect of bone diameter and eccentric loading on fatigue life of cortical screws used with interlocking nails" *Am J Vet Res* 64:569-573 (2003); and Gaebler et al., "A new modular testing system for biomechanical evaluation of tibial intramedullary fixation devices" *Injury* 32:708-712 (2001).

During the development of some embodiments contemplated herein, a more realistic tibial model, involving tapered extremities and based on preliminary measurements, were incorporated into a model to mimic the larger metaphysis. For example, a previous experimental study using a bone model demonstrated that interlocking nails are more susceptible to failure when implanted in the center of larger bones. Aper et al., "Effect of bone diameter and eccentric loading on fatigue life of cortical screws used with interlocking nails" *Am J Vet*

*Res* 64:569-573 (2003). Accordingly, in order to subject an conventional ILN to the most stringent conditions and to allow meaningful comparison between groups, all nails were locked near the extremities of the model (26 mm and 23 mm OD) and were kept centralized using a polyurethane plug. Gaebler et al., "Fatigue strength of locking screws and prototypes used in small-diameter tibial nails: a biomechanical study" *J Trauma* 47:379-384 (1999).

Bone strength has not been shown to be a primary mechanical property that directly affects screw-bone interface alterations during non-failure testing protocols. Szivek J A., "Synthetic materials and structures used as models for bone" In: *Mechanical testing of bone and the bone-implant interface.* An Y H & Drauhgn R A, eds. Boca Raton: CRC Press LLC, pp. 159-171 (2000). Therefore, general mechanical properties of human and canine cortical bone were used as guidelines for choosing an acceptable synthetic testing material. Although human tibia models are available commercially, they are too large to represent tibia of even giant canine breeds (405 to 375 mm long) and they are cost prohibitive for most veterinary studies. A 30% glass filled structural nylon is utilized herein which provides comparable results to a previous study evaluating interlocking nails using canine tibia. von Pfeil et al. "In vitro biomechanical comparison of plate-rod combination and interlocking nail constructs in a canine tibial gap fracture model" *Am J Vet Res* 66:1469-1656 (2005).

Although it is not necessary to understand the mechanism of an invention, it is believed that the larger compliance of the ILNn construct as compared to the ILN8 construct may be attributed to the difference in the solid section core diameter of the nails (i.e., for example, 6 mm and 8 mm, respectively). It is further believed that this resulted in a greater than 3-fold increase in AML It is shown herein that the overall angular deformation of the ILN8 construct was greater than the ILNn construct mainly because of the slack in the ILN8 system. See Example III. Although it is not necessary to understand the mechanism of an invention, it is believed that this slack, which corresponds to the absence of resistance to applied torque, maybe associated with the loose screw-nail interaction. With increasing torque, a rigid interaction between the nail and locking screws of the ILN8 occurs, enabling the ILN8 to resist applied loads. The resulting ILN8 deformation at high torque was similar, although smaller to the overall deformation of the ILNn (~8° and 9.5°, respectively). As with compliance, this difference was attributed to the disparity in the core diameter of the nails. Of note, previous evaluation of a PRC construct in this laboratory shows a similar overall angular deformation to the ILNn in this study 2° and 9.5°, respectively), as well as an absence of construct slack. von Pfeil D et al. "In vitro biomechanical comparison of plate-rod combination and interlocking nail constructs in a canine tibial gap fracture model" *Am J Vet Res* 66:1469-1656 (2005).

In one embodiment, the present invention contemplates an hourglass ILNn design that eliminates instability associated with the use of current unearned ILNs. Furthermore, the improved construct torsional stability matches that of a comparable PRC construct, a device routinely used to treat comminuted diaphyseal fractures. ILNn's as contemplated by the present invention have specific advantages over plate osteosynthesis. For example, an ILNn can be applied from remote locations and used to reduce and stabilize fractures using a closed technique. Such less invasive approaches to a fracture site have been shown to improve early bone healing. Grundnes et al., "The importance of the hematoma for fracture healing in rats" *Acta Orthop Scand* 64:340-342 (1993). Although it is not necessary to understand the mechanism of an invention, it is believed that the combined mechanical and biological benefits of an hourglass ILNn represents an effective and safe alternative to plate osteosynthesis while preserving the advantages of unreamed intramedullary nailing.

Some embodiments of the present invention contemplate optional improvements to the ILNn including, but not limited to:

1) steeper entasis (i.e., for example, a slight convexity or swelling in the ILNn shaft) for a better fit.

2) quick release holes in conjunction with coated SCPs

3) SCP taper surfaces having serrations, threads, or coatings such as, but not limited to diamonds, carbon, or a nylon-type polymer (i.e., for example, polyetheretherketone; e.g., PEEK).

4) hole positioning ranging from between approximately 5-20 mm apart, preferably 10-15 mm apart, and more preferably 11-12 mm apart.

5) ILNn diameter sizes ranging from between approximately 4-15 mm, preferably between approximately 6-10 mm, and more preferably between approximately 8-9 mm.

Interlocking Nail Methods

Bone parts or fragments involved in fractures of long bones, such as the femur, tibia and humerus, are difficult to stabilize satisfactorily. Such instability results in poor healing. Since, for example, the femur and tibia functions as a weight bearing bone, femoral fractures often take longer to heal than other fractures and there is potential for greater complications in setting femoral fractures than there is in non-weight bearing bones. Further, it is known that human patients remaining inactive following surgery have an increased risk of serious complications, including but not limited to, the development of blood clots and pneumonia. Thus, after stabilizing a femoral fracture, early ambulation of a patient is desirable so that the femur will heal quickly and so that the likelihood of complications is minimized.

In treating long bone fractures it is standard practice to use a fixation device adapted to facilitate recovery of the fractured bone. The fixation device provides immobilization of the bone fragments and stabilization of the fractured bone, thus allowing earlier mobilization and weight bearing by a patient. The fixation device is attached to, or inserted into, the bone and cooperates with the bone structure to stabilize the bone. As the bone heals, the fixation device allows the bone fragments to grow together to restore the bone.

A number of different fixation devices, both external and implantable, have been to promote long bone fracture healing. In the past, treatment of long bone fractures consisted of stabilizing the bone portions with plates and screws. However, plates and screws require invasive surgery and, in the case of a femoral fractures, the surgery includes considerable dissection of the thigh in order to expose the fracture for attaching the plates and screws. Invasive surgery, however, can result in a devascularization of the distal portion of the femur leading to a high frequency of complications, including delayed union of the bone sections, osseous fracture and infection. Additionally, due to the muscular stress, recovery from invasive surgery may also involve undesirable post-operative procedures and complications including the bending or breaking of the plates, loosening of the screws and migration of the femoral shaft.

Intramedullary nails have become common for treating many long bone fractures. In its basic faint, an intramedullary nail is rod-like and driven into the bone interior to stabilize a transverse fracture. However, such intramedullary nails often fail to provide effective bone immobilization. Improvements have been made on intramedullary nails to further stabilize the bone by introducing interlocking screws through the nail that are fixed on both sides of the fracture.

Interlocking screws and nails have advantages over plate and screw fixation devices, however, there are still complications. For example, the size of a nail is limited by the diameter of the medullary canal and also by the curvature of the canal. While smaller diameter nails may provide sufficient support, their ends are weakened by any screw holes made through the nail. Smaller screw holes may be used but smaller screws are necessarily weaker. Thus a balance must be maintained between using relatively large nails in relatively large holes which weaken the nail; and using relatively small holes with relatively small screws which weaken the screws.

It is also the case that using the maximum possible diameter nail will occupy most or all of the medullary canal (i.e., containing bone marrow and proliferative bone progenitor cells). This situation results in slower healing because the nail will also prevent the proper blood vessel growth and regeneration within the medullary canal during healing.

Some embodiments of the present invention provide an improved interlocking intramedullary nail and screw that achieve greater fixation and immobilization of fractured bones, while overcoming the deficiencies of other devices and methods.

The present invention contemplates embodiments including, but not limited to, those that; i) relate to improved intramedullary nails; ii) improved screws to secure intramedullary nails in bones; iii) combinations of an improved nail and screw to form an interlocking intramedullary nail and screw combination; and iv) and improved methods for stabilizing fractured bones.

Certain embodiments of the present invention comprise improved intramedullary nails having relatively larger ends and relatively narrower central sections. One of many advantages resulting embodiments of the present invention include, but are not limited to, intramedullary nails that, because of their relatively narrower central sections, fit more easily within the medullary canal of bones and which may more easily be placed in the medullary canal without reaming (i.e., a process that removes most or all of the vasculature in the medullary canal). Although it is not necessary to understand the present invention, it is believed that certain embodiments of the invention are unlike known nails which may fill most or all of the medullary cavity of the bone, destroying the endosteal/medullary blood supply and allowing little or no space for restoration of the blood supply, severely jeopardizing the healing process. While some believe that intramedullary reaming may stimulate new blood vessel growth, the present invention discloses that it is still undesirable to occupy the space needed by the blood vessels with a relatively large diameter nail.

In at least one embodiment of the present invention an intramedullary nail has a generally hourglass shape. Although it is not necessary to understand the mechanism of an invention, it is believed that the hourglass shape will allow the preservation of medullary space between the endocortex and the nail for neovascularization of the diaphysis. Thus, it is further believed that hourglass shaped nails avoid destroying any more vasculature within the bone medullary canal than is needed to provide support. Consequently, removing additional (i.e., unnecessary) bone tissue may jeopardize the bone/nail interface, particularly at the end of the nail, and is likely to result in secondary iatrogenic fractures.

In one embodiment, the present invention contemplates a method comprising placing the hourglass shaped nail in the medullary canal without intramedullary reaming, thereby avoiding unnecessary bone material removal. In one embodiment, the present invention contemplates a method comprising placing the hourglass shaped nail in the medullary canal with intramedullary reaming. Although it is not necessary to understand the mechanism of an invention, the shape of the central section of the nail allows neovascularization.

In one embodiment, the present invention contemplates an hourglass shaped intramedullary nail, wherein the nail accommodates natural bone curvature, including the curvature of the medullary canal, without increasing the diameter of the medullary cavity. In one embodiment, the hourglass intramedullary nail comprise larger ends including at least one conical transverse hole. In one embodiment, the hole may, but need not, be threaded, so as to accommodate surgical screws (i.e., for example, a conical screw) and so as to be more easily secured during a surgical procedure to install a nail/screw arrangement. Although it is not necessary to understand the mechanism of an invention, it is believed that an hourglass intramedullary nail provides the requisite strength for intramedullary placement and with the ability to accommodate surgical screws of a large enough diameter minimizes the likelihood of nail or screw failure.

Figure 3:
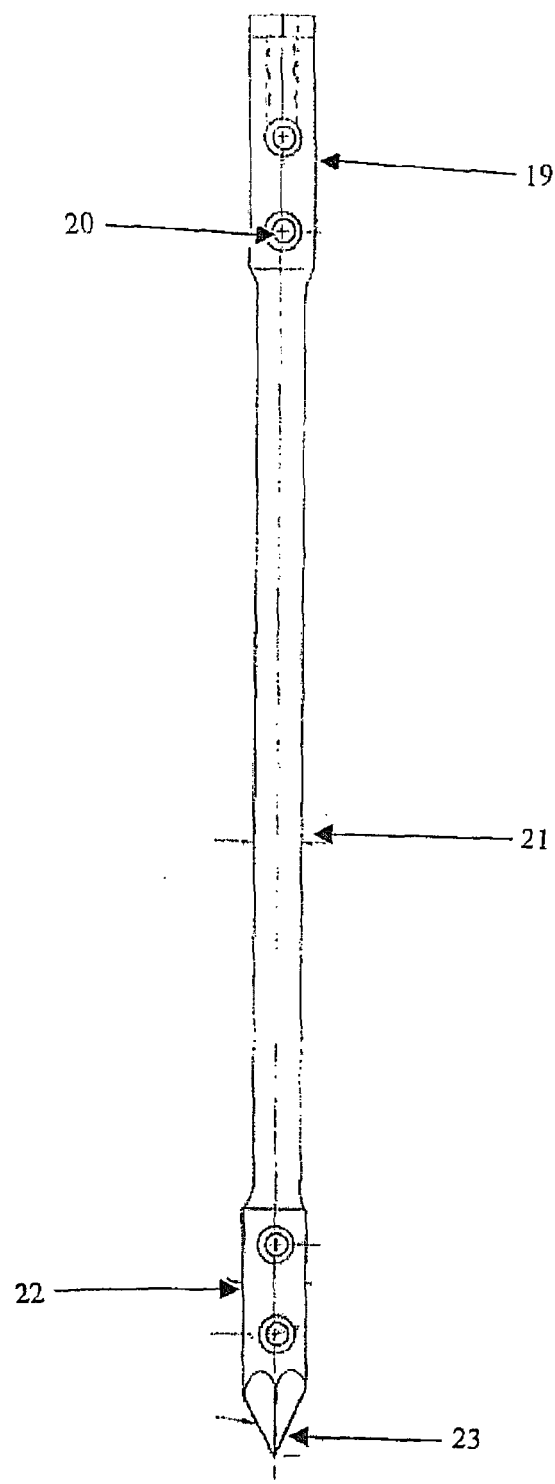
FIG. 3 shows one embodiment of an interlocking nail comprising improvements contemplated herein.

FIG. 3 shows one embodiment of an intramedullary nail contemplated by the present invention. In this embodiment, the nail is substantially cylindrical in shape throughout its length. However, the first end section 22 and the second end section 19 each has a larger diameter than the central section 21. Although not intended to be limiting, FIG. 3 shows one embodiment where the diameter of the first end section 22 and the second end section 19 are substantially the same. The first end section 22, which generally is inserted into bone first, has a trocar tip 23 to allow easy placement. The second end section has a flat threaded end with locking flanges so that force may be applied without damaging the nail. In the shown embodiment, there are two substantially transverse conical holes 20 through both the first end section and the second end section capable of accommodating surgical screws (not shown) which will hold the nail in place in the bone. During placement of this embodiment, one method contemplated by the present invention comprises a nail placed entirely within the bone before being secured by at least one screw.

It is possible, however, to utilize certain embodiments of the invention in a manner wherein a portion of a nail protrudes from the bone. Depending at least on which bone is fractured, the type of fracture, and the size of the bone and the nail utilized, nails placed entirely within a bone may extend only within the bone diaphysis (medullary canal) or may extend from the diaphysis into either the proximal metaphysis or distal metaphysis, or may extend from the proximal metaphysis through the entire diaphysis into the distal metaphysis.

In some embodiments of the intramedullary nail it is not necessary that the diameter of the first end section 22 and the second end section 20 be substantially the same. It is also not essential that the nail be substantially cylindrical. A variety of shapes, including triangular and rectangular nails may work equally well. In such non-cylindrical embodiments, the outer dimensions are less than the diameter of the intramedullary canal. An outer dimension may be determined by the distance between the a nail's midpoint and its further circumferential edge. Also, the number of substantially transverse conical holes may be increased or decreased depending on the needs of the particular patient, and the holes may or may not have threads. The nail also need not have a trocar tip. Depending upon the particular application, it may be preferable to have a trocar tip so that the nail can more easily be placed into the bone. However, other circumstances depending, for instance, on the location of the fracture or the condition of the bone or other tissue, may make it more desirable to use a nail with a rounded or even flat tip. In this circumstance, another instrument may sometimes be used to create a canal for the nail before insertion.

Surgical Screws

Nails contemplated by the present invention may be secured to the bone in manners which include the use of screws. Three exemplary surgical screw embodiments are shown in FIGS. 2A, 2B and 2C.

Figure 2:
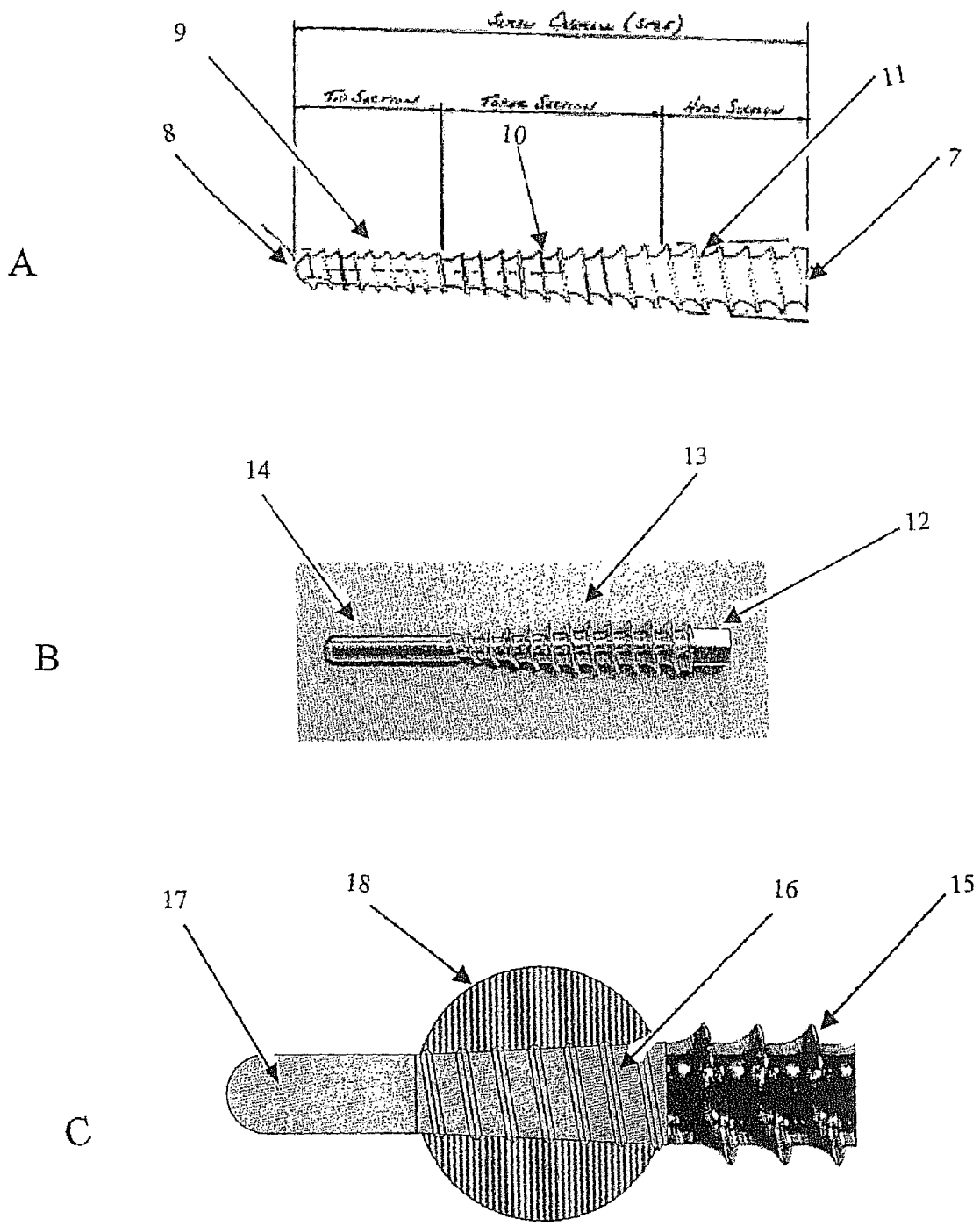
FIG. 2A shows one embodiment of a surgical screw comprising three thread patterns.
FIG. 2B shows one embodiment of a surgical screw comprising one thread pattern.
FIG. 2C shows one embodiment of a surgical screw comprising two thread patterns.

FIG. 2A is a side view of an embodiment of the invention screw which was used to generate test data concerning torsional, bending and compression forces, discussed below. In this embodiment, the cylindrical first end section 9 comprises threads which are relatively closely spaced and have a relatively short height; the cylindrical second end section 11 comprise threads which are relatively widely spaced and have a relatively large height; and the conical central section 10 has threads which are relatively moderately spaced but farther apart than the first end section 9 but closer together than the second end section 11 and have a relatively moderate height that are higher than the threads on the first end section 9 and lower than the threads on the second end section 11. The first, central and second end section diameters are contemplated to be approximately between 2-12 mm, preferably between 4-10 mm, and more preferably between 6-8 mm. This embodiment includes a hexagonal protrusion (not shown at 7) which allows the nail to be inserted with a wrench, ratchet/socket combination or pliers.

The present invention contemplates a method comprising; drilling at least one first hole through the bone cis-cortex, inserting an intramedullary nail comprising at least one transverse conical hole into an intramedullary bone canal wherein the transverse conical hole lines up with the hole; and drilling at least one second hole through the bone trans-cortex in line with the transverse conical hole; rotatably inserting a surgical screw into the bone cis-cortex wherein the insertion continues until the cylindrical first end section was at least partially inserted into the trans-cortex, the conical central section was at least partially inserted into the transverse conical hole, and the cylindrical second end section was at least partially inserted into the bone cis-cortex.

Although it is not necessary to understand the mechanism of the invention, it is believe that both drilling and screw insertion are simplified by the conical shape of the hole in the nail because the relatively larger diameter opening of the hole (due to the conical shape) allows a surgeon, who cannot actually see the nail once it is inside a bone, to more easily "blindly" find the transverse hole with the drill and the screw without the need to rely on radiological guiding, thus reducing the likelihood of exposing medical staff and patients to x-ray radiation, as compared to common practices with cylindrical (non-conical) nail holes and cylindrical nails.

FIG. 2B is a side view of an embodiment of a surgical screw which was used to generate test data concerning the relative strength of solid, unthreaded nail first end sections vs. threaded first end sections, discussed below. In this embodiment, the cylindrical first end section 14 is unthreaded; the cylindrical second end section 13 comprises threads which are relatively widely spaced and have a relatively large height that gradually reduce in size towards the relatively smaller diameter first section end 14. This embodiment includes a hexagonal protrusion 12 which allows the nail to be inserted with a wrench, ratchet/socket combination or pliers.

FIG. 2C is a side view of a third embodiment of the invention screw. In this embodiment, the cylindrical first end section is unthreaded; the cylindrical second end section comprises threads which are relatively widely spaced and have a relatively large height, which are suitable for threading into bone cortex; and the conical central section has threads which are relatively closely spaced and have a relatively small height. The threads on the conical central section may thread into an threaded nail hole; or may cut into a surface of an unthreaded nail hole, particularly in a circumstance where the nail is produced of a harder material than the nail; or the threads may be deformable so that they flatten somewhat tightly lodging the screw into the nail hole when the screw is rotatably inserted. This embodiment may include a hexagonal protrusion which allows the nail to be inserted with a wrench, ratchet/socket combination or pliers; or, alternatively for any of the embodiments discussed herein, an indentation of such a shape so as to accommodate a driving device, such as a flat head screw driver, a phillips head screw driver or a hexagonal key. Although not intended to be limited, some embodiments of the invention comprise screws having either unthreaded or threaded first cylindrical ends; unthreaded or threaded conical central sections which may be sized to fit tightly within conical nail holes so as to lock tightly together with a nail when rotatably inserted therein; and, unthreaded or threaded cylindrical second ends. Although it is not necessary to understand the mechanism of an invention, it is believed that unthreaded screws are stronger than comparably sized threaded screws.

Certain embodiments of the invention, e.g. improved nails, may have advantages even if used with known screws; and certain embodiments of the invention, e.g. improved screws, may have advantages even if used with known nails. In particular, certain embodiments of the invention may allow the use of minimally invasive orthopedic surgical procedures to stabilize fractured long bones, e.g., femur, tibia or humerus, in either human or non-human patients.

In some embodiments of the invention a threaded nail hole comprise deformable threads. In one embodiment, the threads are deformed by the conical central section of a screw during insertion. In another embodiment, the screw threads self-thread into an unthreaded conical nail section wherein the screw is comprised of a material that is relatively softer than the nail.

In some embodiments of the invention the above means, which are representative and not limiting of the numerous manners in which nails and screws may be contacted, will result in a tight fit between the nail and the screw, more particularly, between the substantially transverse nail hole and the screw conical central section. Although it is not necessary to understand the mechanism of an invention, it is believed that this tight fit may result in a particularly stable nail/screw interface, which maintains the position of the nail relative to the screw, and consequently, relative to the bone since one or more screws travel through the bone cortex. It is also believed that this tightly fitting, stable interface between the nail and the screw may result in far better stability for the bone, especially to torsional and bending forces, resulting in significantly shorter healing times.

Unthreaded Screw Sections

In one embodiment, the present invention contemplates an unthreaded screw end having advantageous strength characteristics.

Regardless of the loading mode, i.e. tension, bending or torsion, brittle materials (e.g. surgical steel) fail as a result of tensile stresses. Failure of an implant occurs when that implant reaches its ultimate tensile strength (UTS). The UTS depends on how much stress and strain (or relative deformation) an implant can handle under load.

Stress is a normalized material property, which is proportional to the elastic modulus (E) of the material and also varies with the technique (cold working) used to manufacture that material.

Any factor that decreases the stress level in an implant for a given load will result in a relative increase in the strength of that implant and subsequently will allow that implant to sustain deformations for a longer period of time (i.e. increase the fatigue life of the implant).

Stiffness is a structural property, which defines the ability of an implant to resist deformation. Stiffness is proportional to the elastic modulus (E) of the material and to area moment of inertia (I) of the implant; stiffness is inversely proportional to the cube of the tested length (L) of the implant. The area moment of inertia (I) of an implant depends on its geometry and characterizes the distribution of the material with respect to the axis of applied load. These relationships give rise to the following formula: Bending stiffness=$E*I/L^3$. For screws or solid pegs, the area moment of inertia is directly proportional to the fourth power of the radius (R) of the core of the implant, for example: $I=(\pi*R^4)/4$. Therefore, even a small increase in implant size (diameter) will induce a large increase of the area moment of inertia and of the stiffness of the implant.

When pegs and screws for use with intramedullary nails are made of the same material (surgical stainless steel—316L) and have the same tested length, the only factor that will influence stiffness is the area moment of inertia of the implant, i.e. its diameter. Everything else being equal (E and L), considering a screw and a solid peg of identical external diameter, the peg, having a larger core diameter, will have a larger area moment of inertia and therefore will be stiffer than the screw. Table 2 compares these dimensions in relation to stiffness

TABLE 2

Screw/Peg stiffness as a function of outer dimension.

| Implant | External diam (mm) | Core diam (mm) | AMI (I) | Increase in stiffness |
|---|---|---|---|---|
| Screw | 2.7 | 1.9 | 0.64 | 4 fold |
| Peg | 2.7 | 2.7 | 2.6 | |
| Screw | 3.5 | 2.4 | 1.6 | 4.6 fold |
| Peg | 3.5 | 3.5 | 7.4 | |
| Screw | 4.5 | 3.0 | 4.0 | 5 fold |
| Peg | 4.5 | 3.5 | 20 | |

Under bending conditions (such as occur when a locking screw or a peg is being loaded), bending stress in response to load depends on the tested length (L) of the implant, the force applied (F) to it, the radius (R) of the core diameter of the screw or radius of the peg and the AMI (I) of the implant, for example. Bending stress=$(L*F*R)/I=f(1/R^3)$. Since L and F are constant, R and AMI are the only variables. Thus, again, the AMI is the major variable that influences bending stress. Therefore, at any given load, a small increase in implant diameter (as seen from a screw to a similar sized solid peg) will considerably reduce the stress level in that implant. In other words, for any given load, because of its larger AMI, a peg will sustain a lower stress level than a comparable screw. This is to say that the peg will move farther away from its UTS than the screw, i.e., the peg is a stronger design than a screw.

Figure 4:
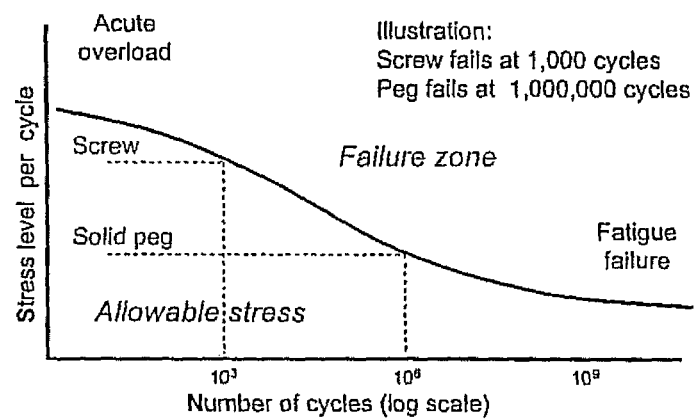
FIG. 4 shows a graphic illustration of the relationship between surgical screw and/or peg stress and failure.

Materials fail as a result of acute over-loads (high stress applied once) or more often as a result of repetitive loads of relatively lower magnitudes (millions of low stress cycles over time). The relationship between the stress magnitude of a given cycle and the number of cycles to which an implant is subjected is described by an S/N curve. FIG. 4 shows such a curve that is unique to each material and characterizes the fatigue life of an implant, i.e., how long the implant will last before failure.

Surgical screws are known to undergo stress during either torsion (i.e., for example, twisting) or bending. FIG. 4 indicates the overall stress pattern that acute overload during bending occurs at a high stress level per cycle after a relatively few number of cycles. Conversely, fatigue failure during bending occurs at a low stress level after a relatively high number of cycles. The "failure zone" (i.e., the area above the curve) is represented in the area between these two extremes where the rate of failure increases over a given number of cycles. In particular, the graph shows that a threaded screw fails before a non-threaded screw (i.e., for example a solid peg). Although it is not necessary to understand the mechanism of an invention it is believed that a non-threaded portion is stronger than a threaded portion because a non-threaded portion has a larger core diameter.

The lower the stress magnitude for any given cycle, the longer the implant will last. For example, when a peg (i.e., for example, an unthreaded screw) is compared to threaded screw, the peg exhibits a longer fatigue life than the threaded screw because the peg is subjected to lower stress levels. It has been shown in vitro that the yielding strength (stress level at which an implant deforms irreversibly) and the fatigue life of a screw were related closely to the inner diameter of the screws, supporting the above equations. Beer et al.: "Analysis and design of beams for bending" *In: Mechanics of Materials* 3rd ed. McGraw-Hill, pp 308-372 (2002); Lin et al, "Bending strength and holding power of tibial locking screws" *Clin Orthop*. 385:199-206 (2001); and Muir et al. "Area moment of inertia for comparison of implant cross-sectional geometry and bending stiffness" *Vet Comp Orthop Traumatol* 8:146-152 (1995).

Surgical Methods

The present invention contemplates placement of the improved interlocking nails using convention surgical technique. In order to verify the procedure, prior to surgery, radiographs of the fractured limb are taken and an appropriately sized interlocking nail is chosen using templates.

Following routine anesthesia the patient is prepared for aseptic surgery using standard procedures. In particular, the entire body, but not the fractured limb, is covered with sterile drapes and the surgeons are masked, caped and gowned in a sterile fashion. All instruments and implants are also sterile.

The femur is exposed preferably via either a small proximal (upper) incision near the hip, or, alternatively, a larger incision over the entire femur is used (avoided if at all possible). The proximal femoral metaphysis is penetrated with a sharp trocar first or directly using one embodiment of an improved interlocking nail as contemplated by this invention. The nail is then slowly and carefully fed into the medullary cavity of the bone. Then continuing through the fracture site into the opposite fragment until the tip of the nail reaches the distal metaphysis. The depth of the penetration is estimated or directly visualized using intra-operative radiography.

In one embodiment, an ILNn comprises a sharp trocar tip. Although this design increases the risk of iatrogenic perforation of the distal cortex (near the knee joint in this case), other ILNn embodiments comprise an hourglass shaped nail and a round tip. Although it is not necessary to understand the mechanism of an invention, it is believed that this round tip pushes the distal fragment away until the length of the limb has been restored without incurring the risk of joint damage.

To facilitate the placement of the nail in curved shape bones (such as the humerus, femur and tibia), reamers may be used to clear a straight path within the medullary canal. The disadvantage of using a reamer is that the cortex may be weakened after reaming (leading to secondary fracture) and that the blood supply of the medullary cavity may be severely jeopardized if the nail fills up the diaphysis.

These disadvantages have lead to recommendations in the art of veterinary medicine to avoid reaming the intramedullary canal. However, in the event that reaming is done, an hourglass shaped nail as contemplated by the present invention leaves space within the medullary canal; and should not interfere with neovascularization.

Figure 8:
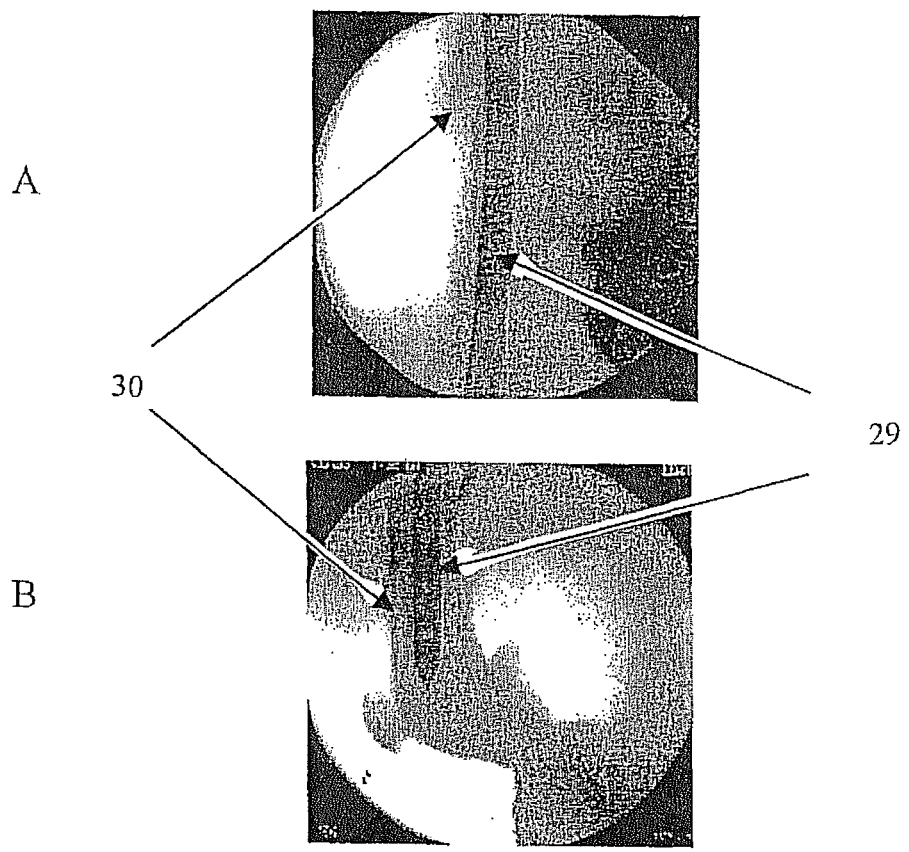
FIG. 8A shows an exemplary intra-operative evaluation of a conventional ILN position from the proximal cranio-caudal view.
FIG. 8B shows an exemplary intra-operative evaluation of a conventional ILN position from distal lateral view.

FIG. 8 shows an intra-operative evaluation of a conventional ILN 29 position from the proximal cranio-caudal view (FIG. 8A) and the distal lateral view (FIG. 8B) after intramedullary insertion into a fractured bone 30. A relatively smaller nail is shown in order to avoid obliteration of the medullary cavity. Larger nails are known to reduce the risk of locking screw failure. An hourglass shaped nail as contemplated by the present invention, however, is designed to take advantage of the larger metaphyses while avoiding over-filling of the medullary cavity. The hourglass shaped nails comprise larger ends, which allow for use of stronger screws, thereby improving the fit within the proximal and distal metaphyses.

Once positioned properly, the nail is linked to a L-shaped alignment fixture or jig that will allow for proper placement of the screws. The jig features 2 arms that can be coupled together. The vertical arm is linked to an extension piece that is connected to the nail. The extension piece protrudes from the fractured bone while the ILN is implanted into the bone. The vertical are of the jig is used to connect the nail and the horizontal arm so that these 2 parts are parallel to each other. The horizontal arm features regularly positioned holes, the positions of which match that of the screw holes in the nail. Small skin incisions are performed at the level of the screw holes in the nail (as indicated by etchings on the side of the jig). Special drill sleeves are introduced through the jig holes and a drill is used to create a hole through the cis-cortex of the bone. The drill bit is then pushed through the nail hole and finally engages the trans-cortex.

Jig offsets between the drill bit tip and the edge of the nail hole may result in drill bit fracture or screw placement off the nail hole. Drill bit fracture or misplacement of the screw has been reported in up to 28% of the screw placement surgeries and may have severe consequences with respect to postoperative morbidity, e.g., bit migration in adjacent joint if not retrieved, increase surgery time and secondary higher risk of infection if retrieved, poor stability and secondary impaired bone healing. Durall et al., "Interlocking nail stabilization of humeral fractures. Initial experience in seven clinical cases" *Vet Comp Orthop Traumatol* 7:3-8 (1994). These intra-operative complications may or may not be seen during surgery. These problems result in increased morbidity due to longer surgery time to retrieve the failed bit, or worse, poor locking of the bone fragment, which increases the risk of non-union. In one embodiment, a conically shaped nail hole reduces, if not entirely eliminates, the occurrence of such complications relative to jig offsets since the drill bit, and thereafter, the locking screw, will be gently funneled into the nail hole.

Following drilling of the cortices, the drill sleeve is removed and a depth gauge is used to measure the length of the screw. The depth gauge is then replaced by a tap sleeve and the cortices are threaded to accept the appropriately sized screw. The tap sleeve is then removed and a screw is driven into the bone cortices and through the nail. The screw length is such that the screw tip will protrude by at least 2 mm on the other side of the trans cortex. This standard technique produces good bone contact and optimizes the holding power of the screw within the bone. The procedure is repeated step by step with, in the case of a nail with 4 transverse holes, the 3 remaining screws. Proper screw position may be ascertained using intra-operative radiography. Although not absolutely necessary, this technique brings peace of mind to the surgeon by providing instant evaluation of the repair and implant position.

To reduce the need for a large inventory of screws with variable lengths, screws may be manufactured, e.g., with one standard length of first end section, which can be cut to the appropriate length after measurement with a depth gauge; and second end sections of varying length.

The use of a larger nail will result in a reduction the working length of the screw and therefore will reduce the risk of cyclic bending failure of that screw. A larger nail will also accommodate larger and stronger conical screws, further reducing the risk of implant failure while improving the stability of the locking mechanism.

Figure 9:
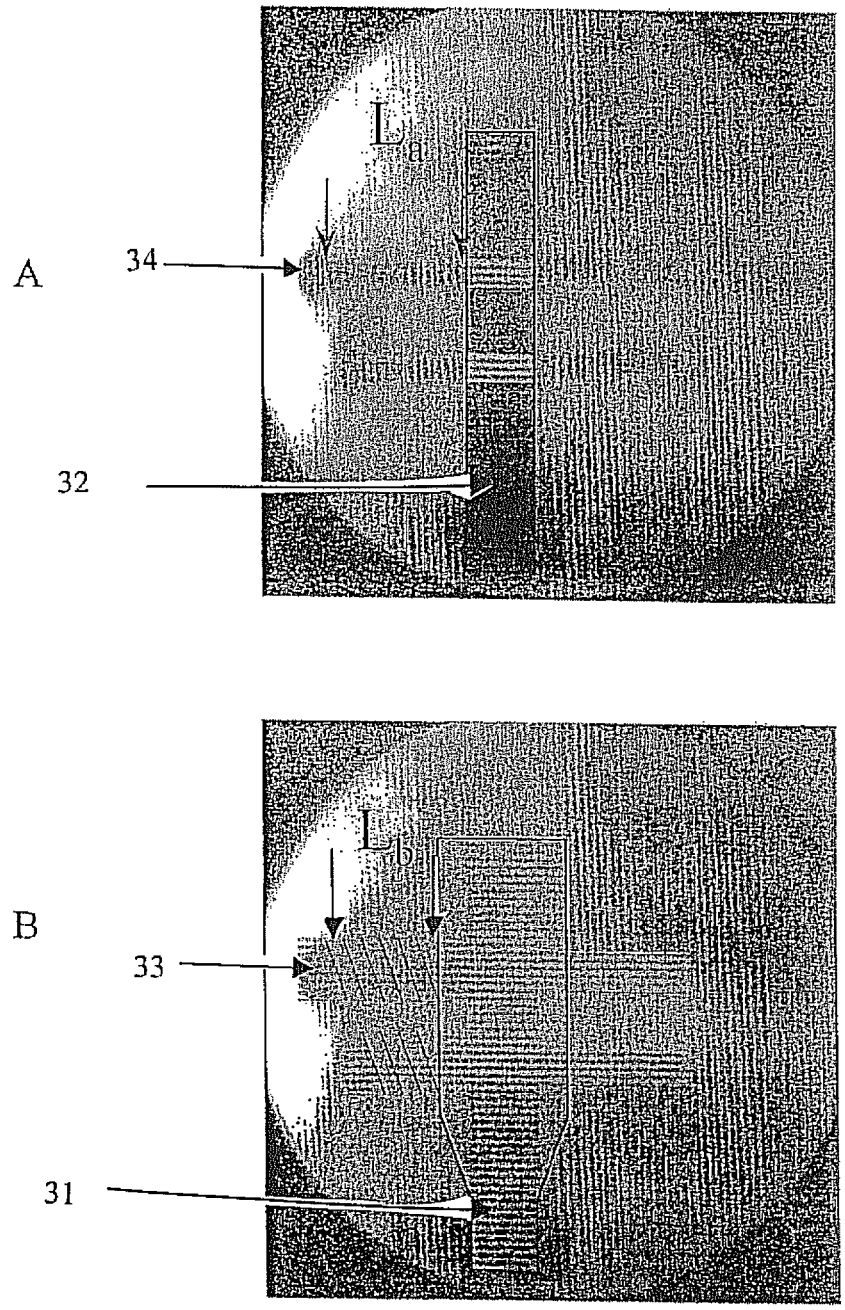
FIG. 9 illustrates how bending stiffness and strength of the screw is inversely proportional to the cube of the working length (L), which runs from the either cortex to the edge of the nail.

FIG. 9 illustrates how bending stiffness and strength of the screw is inversely proportional to the cube of the working length (L), which runs from the either cortex to the edge of the nail. In FIG. 9A two traditional straight screws are shown having a longer working length $L_a$ (as measured between the two arrows) than one embodiment of two conical screws as contemplated herein, having a shorter working length $L_b$ (as measured between the two arrows) depicted in FIG. 9B. Further, FIG. 9 demonstrates the focal increase in diameter of an hourglass ILNn 31 versus a conventional ILN 32, wherein $L_b$ is smaller than $L_a$. Therefore, a conical screw 33, as contemplated herein, with working length $L_b$ will be subjected to less bending stresses than a conventional straight screw 34 with working length $L_a$. In addition, the bending stiffness, and therefore strength, of the screw is proportional to the 4th power of the screw radius. In this example, a 4.5 mm conical screw would be used rather that a 2.7 mm straight screw. Further, the conical screw would feature a solid peg with a diameter of at least 3.2 mm compared to the 2.5 mm core diameter of the standard 3.5 mm straight screw or the 1.9 core diameter of the standard 2.7 mm straight screw.

Figure 10:
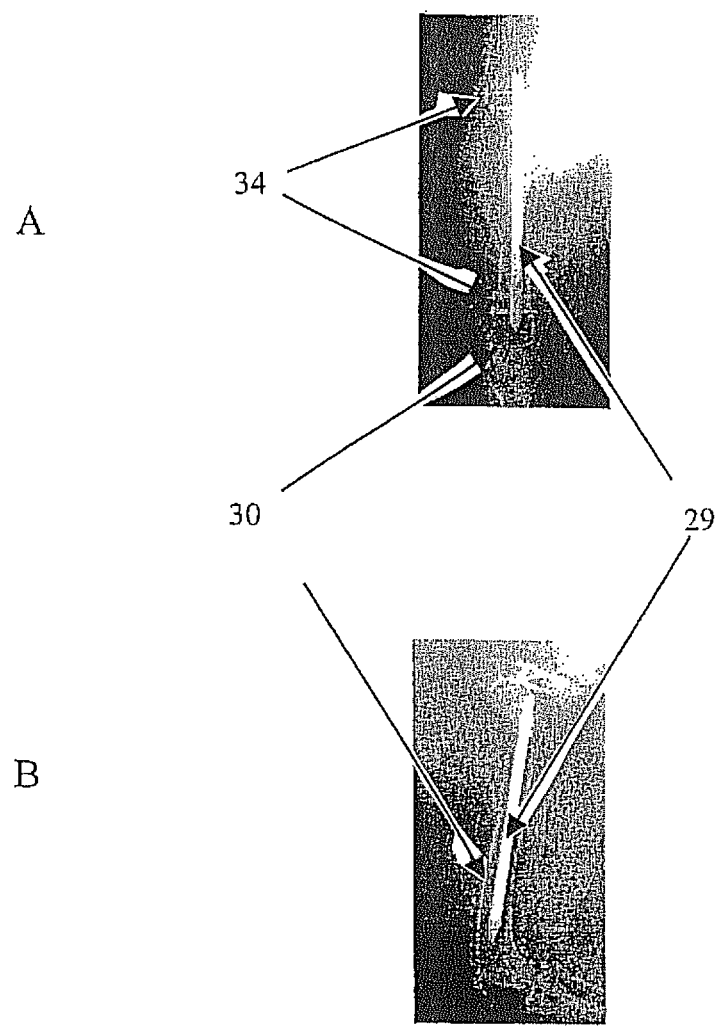
FIG. 10A shows an exemplary cranio-caudal radiographic view of a repaired femur using a conventional ILN. Note that the large callus formation and the persistence of a fracture gap indicate local motion, which is responsible for slow healing.
FIG. 10B shows an exemplary lateral radiographic views of the repaired femur using a conventional ILN. Note that the large callus formation and the persistence of a fracture gap indicate local motion, which is responsible for slow healing.

At the conclusion of the implant procedure, post-operative radiographs are taken under anesthesia to confirm limb alignment, fragment reduction if appropriate and, implant position. FIG. 10 shows crania-caudal (FIG. 10A) and lateral (FIG. 10B) radiographic views of a repaired fracture bone 30 with a conventional ILN 29. Medullary canal fill is appropriate for a healthy recovery despite using relatively small straight screws 34. A disadvantage of small screws is that they jeopardize post-operative stability, particularly in a young, active, intact male. In one embodiment, the use of an hourglass nail would be optimal since it strengthens the locking mechanism and therefore post-operative stability while preserving the medullary blood supply and therefore the healing potential of the bone.

Follow-up clinical and radiographic evaluation is recommended at 6 weeks then 6 months and one year post-operatively. The implant is most often left in place although removal may be performed.

In one embodiment, the present invention also contemplates a method to place an ILNn 35 using a handle driving device 49 and an alignment jig 50. See FIG. 18. In one embodiment, prior to ILNn implantation, the ILNn 35 is coupled to an extension piece 48 that links the ILNn 35 to an alignment jig 50. In one embodiment, the alignment jig 50 stays outside of the bone during the locking procedure while ILNn is inside the bone (not shown).

Figure 18:
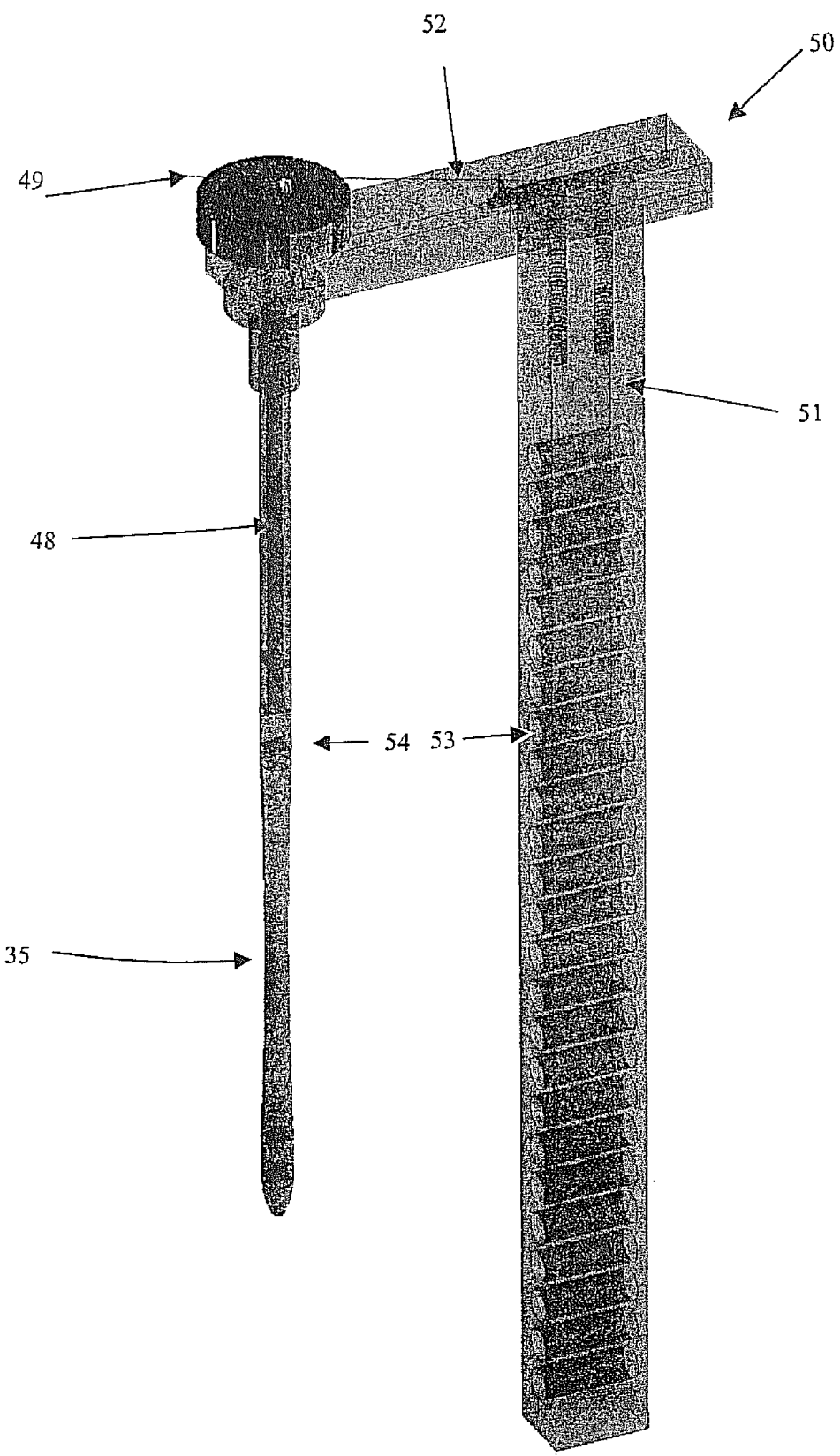
FIG. 18 shows one embodiment of an ILNn 35 coupled to an extension 48 and a driving handle device 49 attached to an alignment jig 50.
Figure 19:
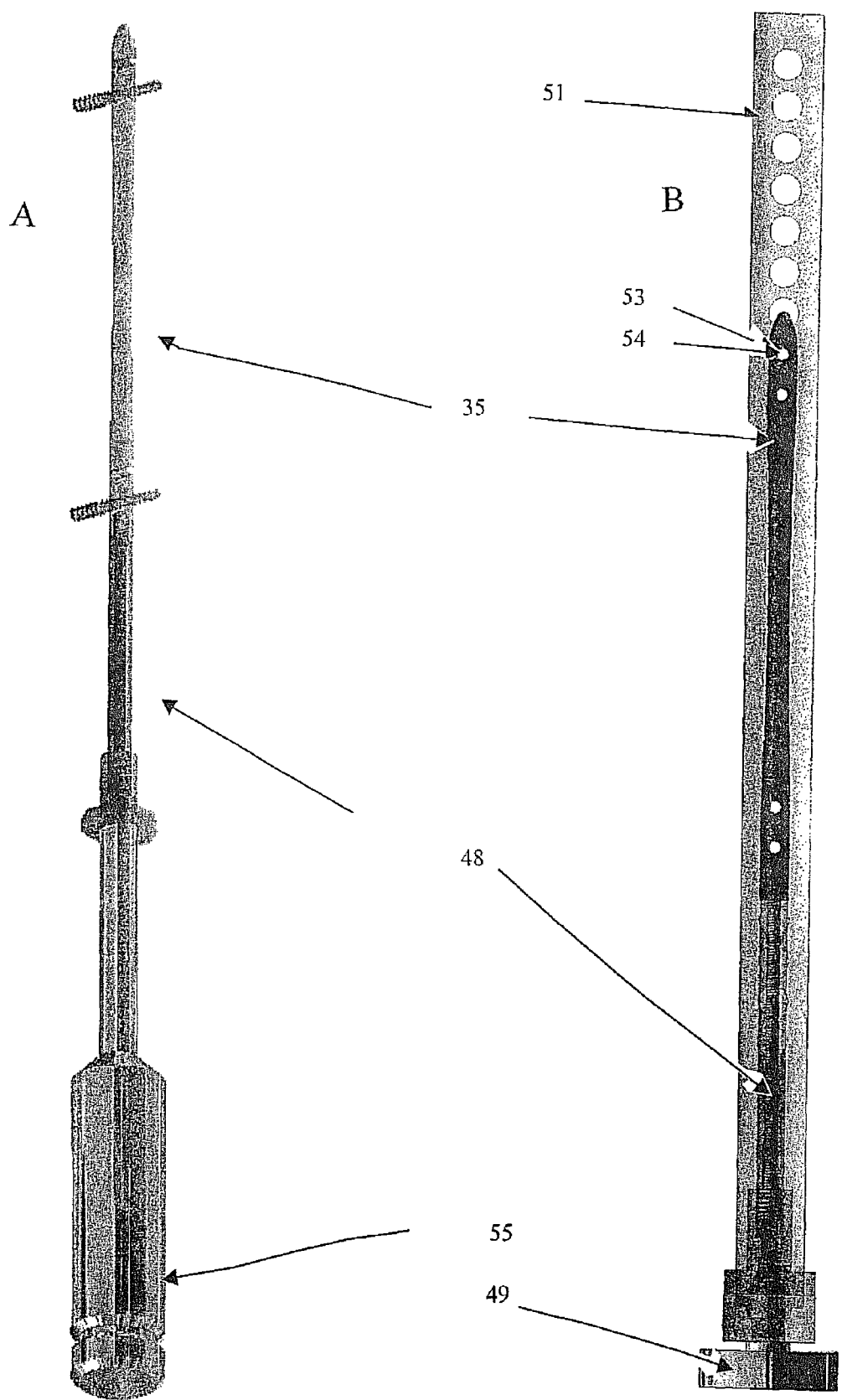
FIG. 19 shows isolated views of Panel A depicting one embodiment of a coupled ILNn 35 to extension piece 48 and driving handle 49 and Panel B depicting one embodiment of an ILNn 35 alignment as depicted in FIG. 18, showing the superimposed ILNn hole 54 and horizontal arm 51 alignment hole 53, wherein the ILNn 35 is coupled to an extension piece 48 and a driving handle device 55.
Figure 20:
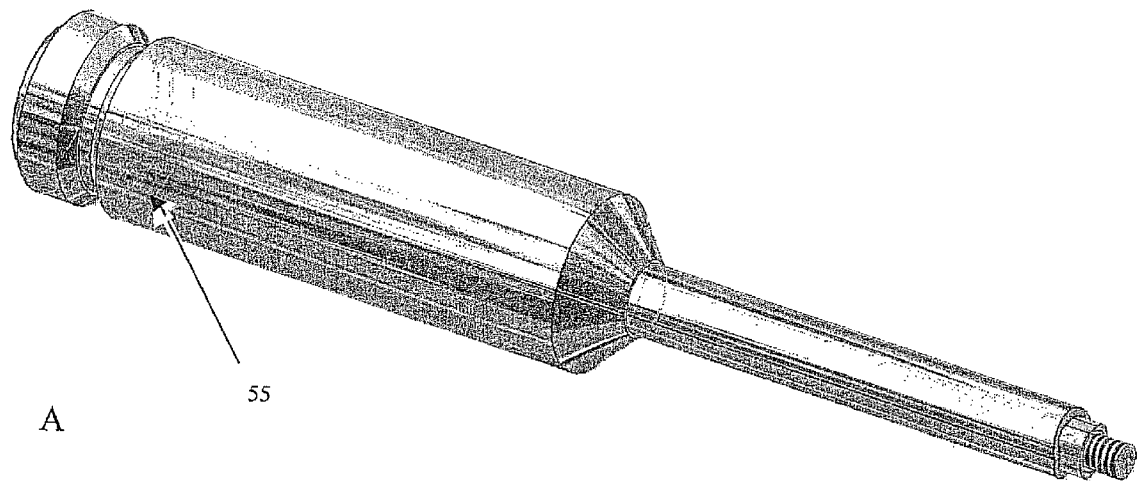
FIG. 20 shows two embodiments of a driving handle device. Panel A shows a close-up view of driving handle device 55 as shown in FIG. 19B. Panel B shows a close-up view of driving handle device 49 as shown in FIG. 18 and FIG. 19A.
Figure 20:
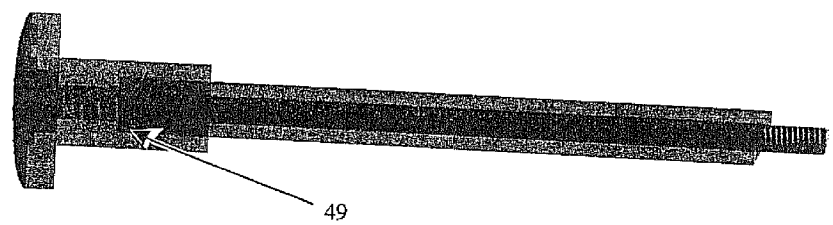

Using FIG. 18 as an example, the method comprises the following steps:

1) coupling an ILNn 35+extension piece 48 to a handle driving device 49 via matched threaded portions on the extension and ILNn;
2) inserting the coupled handle driving device 49 into the bone (not shown);
3) decoupling the coupled handle driving device 49 from the extension piece 48+ILNn 35;
4) coupling the inserted ILNn 35+extension piece 48 with a vertical arm 51 of an alignment jig 50;
5) coupling the vertical 51 and horizontal 52 arms (adjustable) of the alignment jig 50;
6) inserting a first drilling sleeve (not shown) in appropriate holes 53 on the horizontal arm 52 such that the position of each hole 53 on the horizontal arm 52 matches that of a corresponding hole 54 in the ILNn 35;
7) drilling hole #III into the cis cortex to 4 mm; removing first drill sleeve and inserting a second drilling sleeve and then drilling into the transcortex to 3.2 mm;
8) removing drill bit and sleeve;
9) inserting locking peg into hole;
10) repeating steps 6-9 for holes II, IV, and I (with locking pin III in place);
11) removing horizontal arm of the aiming fixture;
12) removing locking pin III;
13) measuring transcortex/nail SCP threaded length and nail/cis cortex SCP peg length with a depth gauge;
14) selecting SCPs for measured threaded length and cutting pegs in to appropriate length;
15) inserting and locking SCPs;
16) repeating steps 12-15 for holes II, IV, and I;
17) closing surgical incision.

EXPERIMENTAL

The following are examples of specific embodiments contemplated by the present invention. They are not intended to be limiting and are described only provide an illustration as understood by one skilled in the art. Some abbreviations used herein, include: ILN: Conventional interlocking nail; PRC: Plate Rod Combination; Bo: Bolts used as a locking devices; Sc: Screws used as a locking devices; Hb: Hybrid nail; To: torsion; and Be: bending.

Example I

ILNn, Conventional ILN, & PRC Cross-Comparison Using a Synthetic Bone Model

The purpose of this study is to compare the biomechanical properties one embodiment of the interlocking nail design to: 1) currently available ILNs using screws or bolts and 2) to a PRC using a gap fracture model.

A synthetic bone substitute represents canine tibiae. Specimens will be divided into 6 groups (n=12/group) and instrumented with either a 6 mm or an 8 mm conventional ILN with screws or bolts, a 6 mm novel conventional ILN with novel screws, or a PRC. To mimic a comminuted fracture, a 60 mm mid-diaphyseal defect will be created in all specimens. Specimens will be tested in either torsion, compression, or 4-point bending (n=4/testing mode) using an Instron machine.

In an attempt to limit specimen variability and to circumvent the increasing difficulty of procuring canine bones, a synthetic tibial model will be custom made from an E-glass-epoxy composite material (SAWBONES®, Pacific Research Labs, Vashon, Wash.). This material, which has been developed to have material properties similar to those of cortical bone, has been used as a bone substitute model. The specimens will be manufactured to a length of 210 mm, with an inside diameter of 9 mm and a wall thickness of 3 mm, based on a previous study performed in our laboratory using actual canine tibiae.

Commercially available ILNs will be obtained from Innovative Animal Products (Rochester, Minn.) while the novel ILNs will be manufactured by BioMedtrix (Boonton, N.J.). All other implants (LC-DCP, screws, IMR) will be obtained from Synthes (West Chester, Pa.).

Two "osteotomy" lines, 60 mm apart, centered on the middle of the specimen will be etched on the surface of each synthetic tibia using a Dremel circular saw. Implants will be applied to the synthetic tibia in 6 groups for a total of 12 specimens per group as follows:

Group 1 (ILN6s): 6 mm×160 mm conventional ILN with four bicortical 2.7 mm screws
Group 2 (ILN6b): 6 mm×160 mm conventional ILN with four 2.7 min bolts
Group 3 (ILN8s): 8 mm×160 mm conventional ILN with four bicortical 3.5 mm screws
Group 4 (ILN8b): 8 mm×160 mm conventional ILN with four 3.5 mm bolts
Group 5 (ILNn): novel conventional ILN and screws
Group 6 (PRC): 4 mm IMR with an 11 holes 3.5 mm LC-DCP secured with 6 bicortical 3.5 mm screws Using a custom designed fixture, the ILNs will be accurately centered in all specimens. The IMR diameter is such that it fills approximately 40% of the specimen inside diameter. It has been suggested that this ratio may represent an optimal compromise between improvement of the biomechanical properties of the PRC construct and the preservation of beneficial axial microstrain at the fracture site. To mimic a comminuted fracture, following implantation of either device, the 60 mm central "ostectomy" will be completed along the previously etched lines taking care not to damage the implants.

Specimens will then be potted using epoxy in a custom-designed embedding fixture. The geometrical characteristics of the fixture will match those of the loading jigs thus ensuring that 1) the conventional ILN or IMR axis will accurately coincide with the rotation axis (torsional testing) of the Instron testing machine, 2) the tested length (length of exposed specimen between potting cups) will be consistent in all specimens, and 3) the tested length of all specimens will be centered between the loading jigs.

Using dedicated custom designed loading fixtures all specimens will be mounted in an Instron servo-hydraulic testing machine coupled to a 500 lb. load cell. Initially, specimens will be tested non-destructively in either compression, 4-point bending or torsion (n=4 per testing protocol).

The non-destructive tests will be run in load control for 10 cycles. Measurements consisting of actuator displacement and corresponding load will be studied in the 10th cycle.

Compression tests will be run using a haversine waveform to a peak load of 176 N, equivalent to 60% of the mean body weight (30 kg) of a mid-size dog. This load level was chosen to simulate post-operative loading conditions. The load is slightly less than the force acting on a healthy canine hind limb during trot. Compression will be applied along the axis of the conventional ILN or IMR.

Bending tests will be run using a sinusoidal waveform with a bending moment of 3.5 Nm. The bending moment chosen in this study is identical to that used in a comparable biomechanical evaluation of external fixation devices in a gap fracture model. A specially redesigned fixture will allow for application of a constant bending moment over the entire bone model/implant construct, as well as alternate bending in the medio-lateral and latero-medial directions. In addition, experiments will be performed by directly loading the bending fixture cups. This innovative method limits the risk of punctual pressure peaks, which could lead to iatrogenic sample failure. It will also allow a true representation of the construct deformation under bending stresses.

Torsion tests will be run using a 0.125 Hz sinusoidal waveform with a torque level of ±5 Nm. This frequency was established in pilot tests in our laboratory and is based on the frequency that generates minimal electrical noise in the response of the constructs to load during testing. The torque level used in this study is identical to that used in a previous biomechanical investigation. Torsion will be achieved using a pinion assembly system that converts the linear displacement of the servo-hydraulic actuator into rotation of the proximal cup while the distal cup remains static.

The destructive tests will be run in position control to construct failure. Compression testing to failure will be run at 100 mm/sec. Bending tests to failure will be run at 25°/sec. Torsion testing to failure will be run with a ramp rate of 180°/sec. These rates were established in a previous study supported by the CAFI8 and will be confirmed in a pilot test with the synthetic tibiae.

Sample sizes were determined using a power analysis (power>0.9) based on means and standard deviations obtained during preliminary experiments.

A load cell coupled to the Instron actuator will record loads (N) over time while actuator displacement (mm) will be recorded simultaneously at a sampling rate of 50 Hz (torsion) and 500 Hz (compression & bending). Since all constructs will be tested under load control conditions during nondestructive testing, construct compliance rather than stiffness will be evaluated. Construct compliance is the inverse of stiffness and is defined as the slope of the deformation versus load curve. Construct compliance will be determined in the 10th cycle using linear regression with a $r^2$ value greater than 0.95. Construct linear deformation will be obtained from actuator displacement data (compression) while construct annular deformation will be computed from the geometrical dimensions of the bending and torsion jig.

Based on the results of a pilot study compliances were bimodal with substantially different slopes at low and high loads/torques, especially under bending and torsion conditions.

Example II

ILNn, Conventional ILN, & PRC Cross-Comparison Using a Synthetic Bone Model

This example provides biomechanical data with a direct comparison between screwed or bolted conventional ILN systems and a novel conventional ILN design.

A tibial bone model consisting of PVC tubes was used. The tubes were custom worked to have a total length of 210 mm, an inside diameter of 9 mm and a wall thickness of 3 mm. These dimensions were used to mimic respectively the mean length, medullary cavity diameter and cortical thickness of canine tibiae used in a previous similar study (CAP #81-2156-D). Bone models were divided into 6 groups (n=2/group) and were implanted with either one of the following:

Groups 1 & 6 mm×160 mm conventional ILN with 4 bicortical 2.7 mm screws (ILN6s) or bolts (ILN6b)

Groups 3 & 4: 8 mm×160 mm conventional ILN with 4 bicortical 3.5 mm screws (ILN8s) or bolts (ILN8b)

Group 5: Novel conventional ILN and screws (ILNn)

Group 6: 4 mm×228 mm IMR combined with an 11-hole, 3.5 mm bone plate (PRC)

All implants were centered exactly on the mid-point of the specimen. To mimic a comminuted fracture, a 10 mm mid-diaphyseal defect was created with a bone saw in all specimens following implant fixation. Potted specimens were mounted in an Instron testing machine using simple fixtures from a previous study. Specimens were cyclically loaded for 10 cycles in either 4-point bending (3.5 Nm), compression (176 N), or torsion (±5 Nm). These loading conditions were chosen from a previous study investigating the biomechanical properties of intact tibiae of similar sizes (torsion and bending), and to mimic the compressive loads placed on the hind limb at the trot. Since constructs were tested under load control conditions, compliance rather than stiffness was evaluated. Construct compliances, defined as the slopes of the deformation versus load curves, were determined at the 10th cycle, then qualitatively compared within and between constructs.

One specimen from each of the ILN6b, ILN8b, PRC and ILNn groups had the osteotomy increased to 60 mm in order to evaluate a larger gap fracture model representing a larger comminution. The results appeared similar to the 10 mm gap model. Thus the larger gap will be used in the proposed study, as it is more relevant to the size of comminuted fractures seen clinically.

Compliance curves for all currently available conventional ILN constructs were bimodal in compression, bending and torsion. This finding indicates that "play" or "slack" is present in these currently available conventional ILN systems (See FIG. 5B). The vertical portion of the graph characterizes the slack present in those conventional ILN systems. The slack represents the initial deformation of the construct under an applied load (i.e., for example, torsional stress), prior to engagement of the locking screws/bolts on the nail. While all traditional ILNs exhibited similar bimodal compliances in both torsion and bending, ILNn and PRC constructs showed typical unimodal compliances for both test types. Unimodal compliances indicate continuous resistance to torsional and bending stresses.

Figure 5:
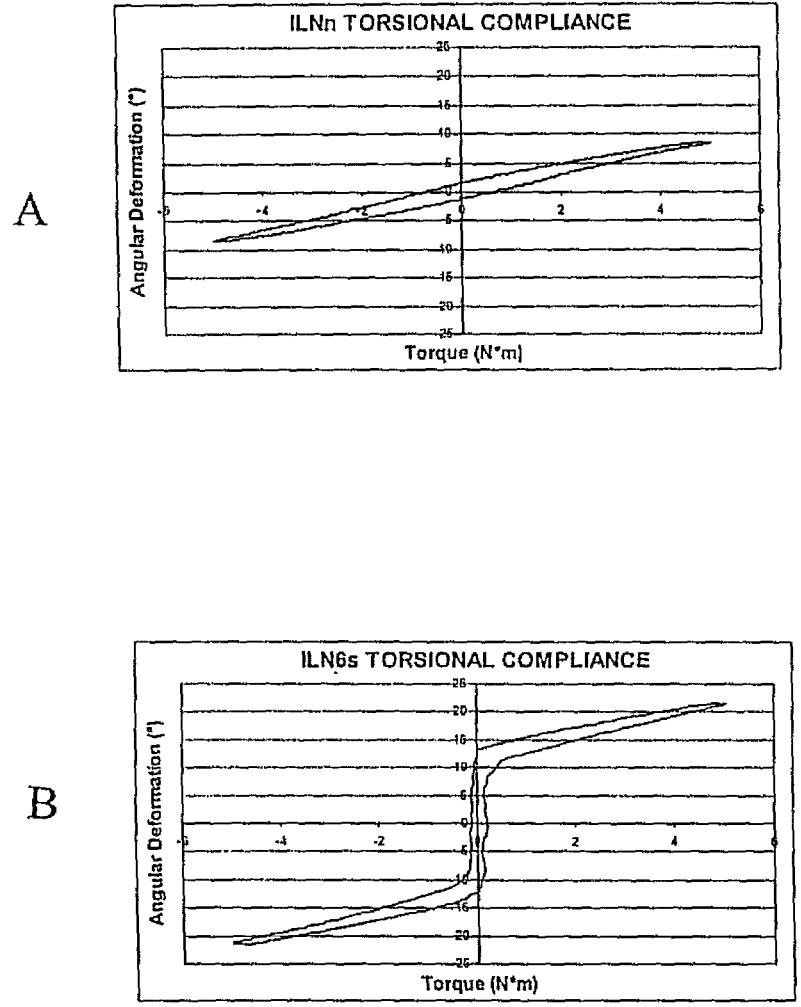
FIG. 5A presents a representative torsional compliance graph of one embodiment an improved interlocking nail (ILNn; i.e., new ILN) contemplated by the present invention.
FIG. 5B presents a representative torsional compliance graph of a commercially available interlocking nail (ILN6s; i.e., a 6 mm ILN (diameter) locked with screws).

In one embodiment of the present invention, ILNs show unimodal compliance (i.e., for example, FIG. 5A; ILNn). Although it is not necessary to understand the mechanism of an invention, it is believed that unimodal compliance indicates a continuous resistance to torsional and bending stresses. In one embodiment, the construct deformation differs between by approximately 25° (i.e., for example, a commercially available ILN6s (~40°) versus one embodiment of the present invention ILNn (~15°)).

Figure 6:
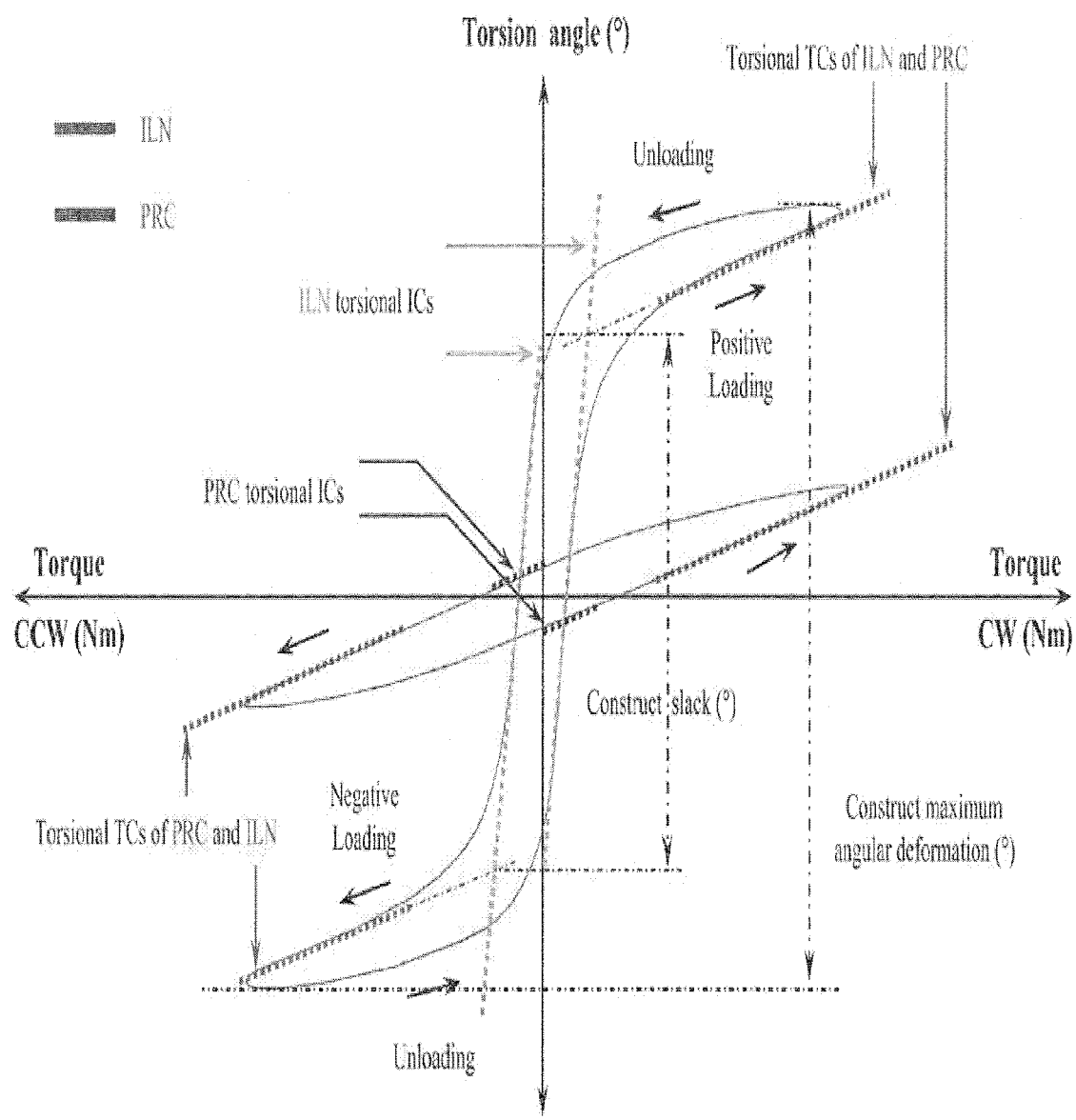
FIG. 6 presents a representative torsional compliance graph showing both a commercially available interlocking nail (conventional ILN; the sigmoid curve) and one embodiment of an improved interlocking nail contemplated by the present invention (i.e., a plate-rod construct (PRC) comprising an hour-glass shaped intramedullary nail and/or rod; the elliptical curve).

During the slack phase there is no resistance by the construct to the applied load (FIG. 6). FIG. 6 presents an integrated comparison of additional torsional data. The sigmoid curve demonstrates the characteristic bimodal behavior of a commercially available conventional ILN bone construct (ILNbc). The elliptical curve shows the homogenous behavior of a plate rod construct (PRC) improved by one embodiment of the present invention (i.e., for example, an hour-glass shaped intramedullary nail and/or rod). The steep initial compliance (IC) of the ILNbc demonstrates that large angular deformations occur as the construct goes from clockwise (CW) to counter-clockwise (CCW) rotation and vice versa. This deformation, which is associated with virtually no change in torque magnitude, reveals the transient slack of the ILNbc. Although it is not necessary to understand the mechanism of an invention, it is believed that the PRC holds consistent compliance of the constructs throughout the torsion cycle because of the improved design as described herein. In particular, maximum angular deformation (i.e., represented by fill CW to full CCW rotation), of the traditional ILNbc was greater than that of the ILNn and PRC.

Figure 7:
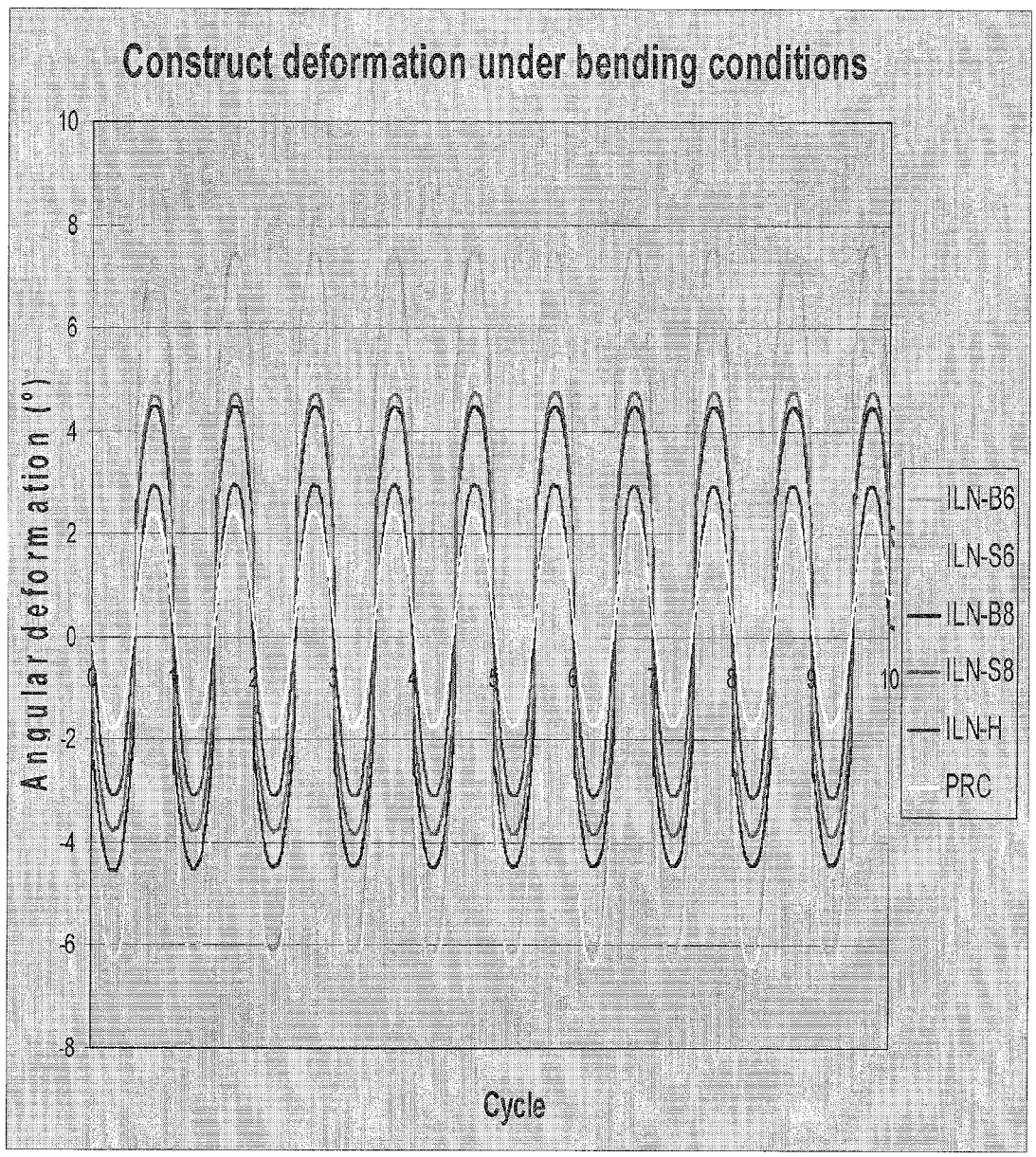
FIG. 7 presents comparative representative data during nail bending tests.

Importantly, while all constructs experienced subtle and similar deformation in compression, angular deformation in bending and torsion of the ILNn or PRC was less than half that of the similar sized traditional ILN6s and ILN6b and approximately 30% less than that of the larger ILN8s or ILN8b (FIG. 7).

FIG. 7 presents a graphical representation of the angular deformation of several embodiments of conventional ILN bone constructs during bending (left) as well as actual angular deformation under bending and torsional conditions. The quantitative relationships supporting FIG. 7 are presented in Table 3. Note the similar magnitude of angular deformation between the ILNn and PRC constructs as well as the absence of slack in either system regardless of the loading environment.

TABLE 3

Relationship of Bending Deformation and Construct Slack

|  | Max. bending deformation (°) | Construct slack (°) |
| --- | --- | --- |
| ILN-B6 | 13.73 | 5.06 |
| ILN-S6 | 11.80 | 4.40 |
| ILN-B8 | 8.93 | 3.88 |
| ILN-S8 | 8.57 | 3.83 |
| ILN-H | 6.00 | 0.00 |
| PRC | 4.10 | 0.00 |

|  | Max. torsional deformation (°) | Contruct slack (°) |
| --- | --- | --- |
| ILN-B6 | 30.20 | 11.30 |
| ILN-S6 | 42.80 | 26.25 |
| ILN-B8 | 20.52 | 6.83 |
| ILN-S8 | 32.80 | 17.00 |
| ILN-H | 16.78 | 0.00 |
| PRC | 18.20 | 0.00 |

The results suggest that while all conventional ILN and PRC constructs are equally capable of resisting compression, PRC and ILNn constructs may be more stable in rotation and bending. Since rotational and bending forces are deleterious to bone healing and implant fatigue life, the ILNn construct may represent a better alternative to currently available ILNs in the treatment of highly comminuted fractures.

Example III

Torsional Analysis of an Hour-Glass Shaped Conventional ILN

This example compares a commercially available ILN8 (8×185 mm) that is used to treat comminuted tibial diaphyseal fractures in the most common dog in our practice, mongrel dogs weighing approximately 30 kg, to comparably sized embodiment of an ILNn using an SCP (i.e., an ILNn-SCP system) as contemplated herein.

The ILNn-SCP system used in this example meets the following constraints:
1) Provides a rigid interaction with the nail.
2) The shape limits interference with endocortices and limits the risk of distal joint infraction while facilitating fracture reduction.
3) The shape and size facilitates successful insertion during surgery.

Secondary constraints related to addressing theoretical stiffness and strength of the ILNn-SCP system, were also considered in the design, including, but not limited to:

1) An AMI<a 4.5 mm bone screw and/or comparable to a 3.5 mm bolt.
2) An AMI at the level of a locking hole similar to that of an 8 mm nail using 3.5 mm bone screws in both the mediolateral and craniocaudal planes.
3) An AMI at the weakest part of the novel nail central solid section had to be similar to that of the solid section of a 3.5 mm br-DCP.

Figure 11:
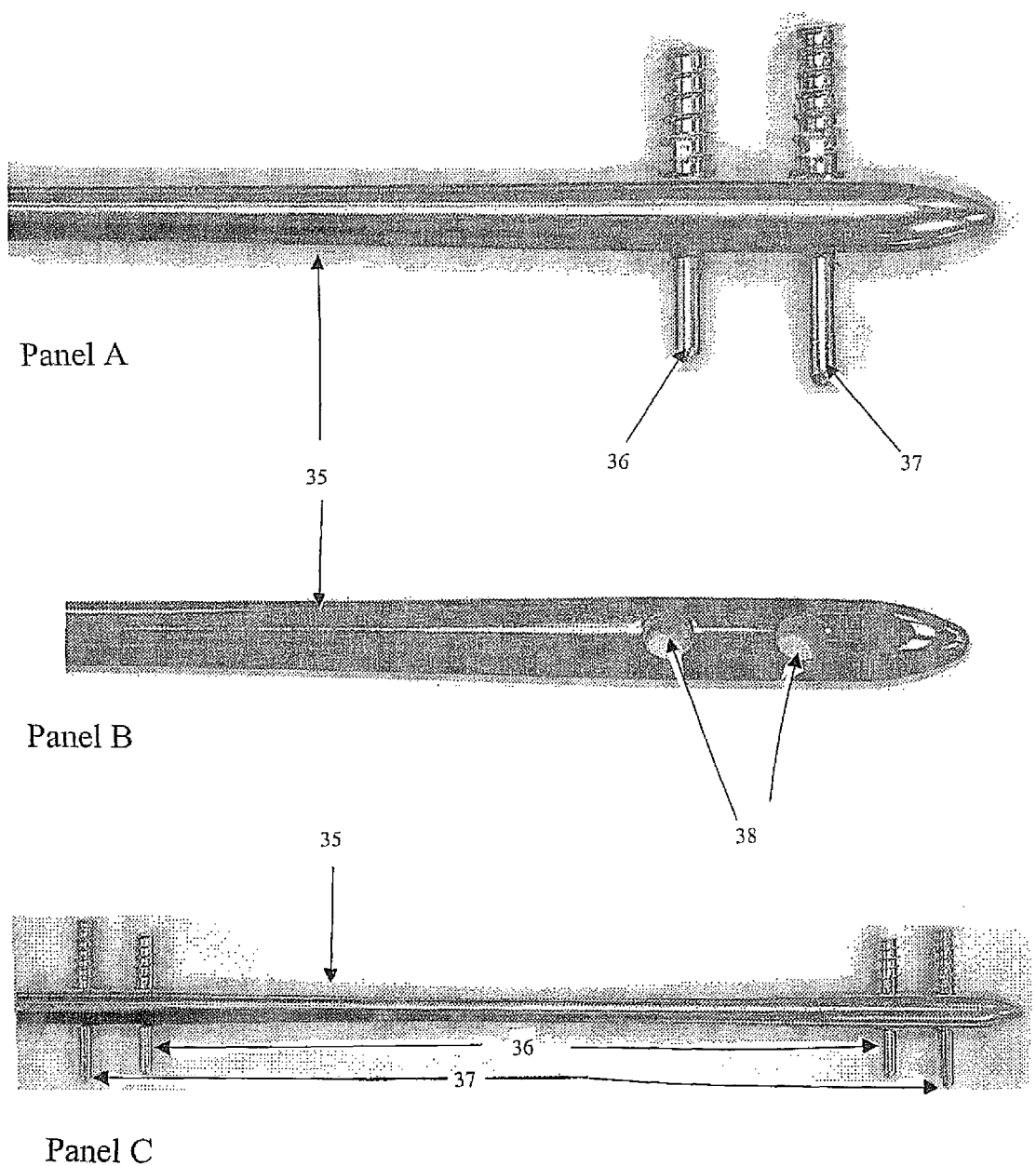
FIG. 11 shows one embodiment of a blunt ended hourglass ILNn 35. Panel A provides a close-up version of a blunt end ILNn 35 with a first conical screw 36 and a second conical screw 37. Panel B provides a close-up version of the blunt end showing two substantially transverse conical holes 38. Panel C provides a plan view of the ILNn 35 having two first conical screws 36 and two second conical screws 37.

These constraints were met by designing an hourglass-shaped nail featuring an oblong bullet-like distal blunt tip ILNn in combination with a locking SCP devices (FIGS. 11A, 11B, & 11C). Both embodiments were manufactured out of 316-L stainless steel. The outside diameter (OD) of the nail extremities was 8 mm while the central portion featured a reverse entasis reducing the middle nail OD to 6 mm. Two tapering nail holes (4 mm OD and 0.05 taper) were placed 11 mm apart in each nail extremity. The extreme holes were separated by 155.5 mm. The SCP was designed as a self-tapping screw (4 mm core diameter) with a central Morse taper matching the nail hole and a solid 3.2 mm OD distal tip. Prototype SCPs were manufactured in two lengths (28 mm and 30 mm).

Area moment of inertia—Using established methods, AMIs were calculated at the level of the various sections of the SCP and at the level of the nail hole and central section for the ILNn.

Bone model preparation—A synthetic tibial model was custom made from 30% glass filled, structural nylon. Nylon is known to have material properties similar to those of cortical bone (Table 4).

TABLE 4

Comparative composite material properties cortical bone models

| Property | Human cortical bone range | Canine cortical bone range | 30% glass filled structural nylon[vii] |
| --- | --- | --- | --- |
| UTS (MPa) | 53-135; 106.8[i] | NA | 65-195; 140 |
| UCS (MPa) | 145.1-166.7; 158.8[i] | 112.8[v] | 140 |
| USS (MPa) | 68[ii] | NA | 59-85; 72 |
| Young's modulus: E (GPa) | 8.2-17; 14.9[iii] | 12.26[v] | 7.2 |
| Poisson's ratio | 0.46-0.58; 0.49[iii] | NA | 0.35 |
| Density (g/cm$^3$) | 1.9[iv] | 0.84[vi] | 1.35 |

Figure 12:
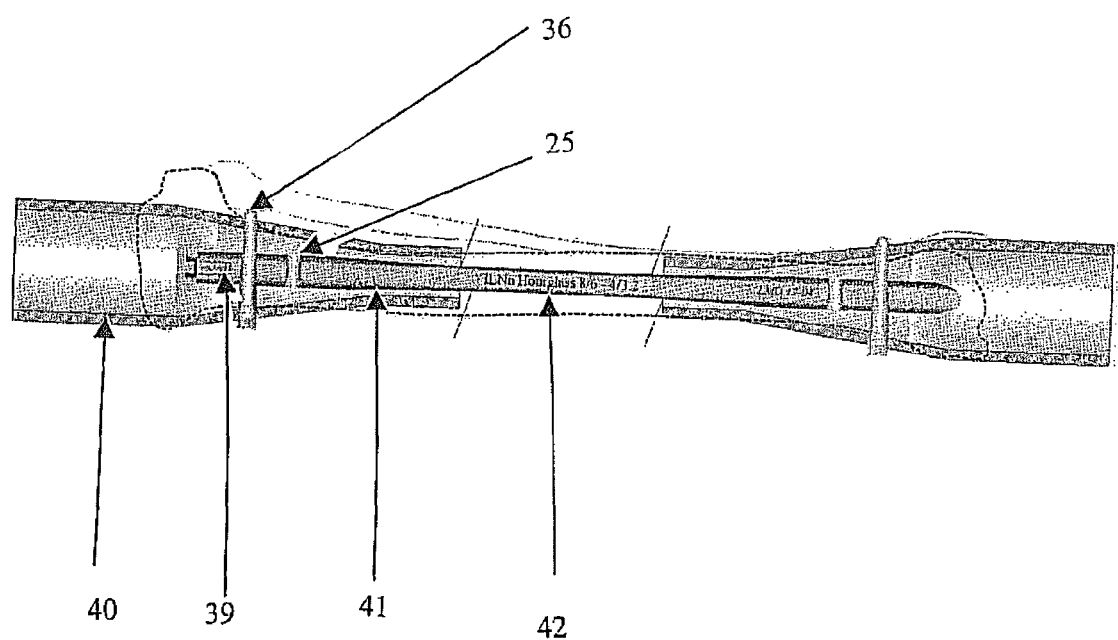
FIG. 12 illustrates one embodiment of a synthetic bone model that mimics the dimensions of the tibia of a 30-35 kg dog (see dotted outline) using a 30% glass filled nylon composite. An outline of an actual tibia/fibula is superimposed over the bone model showing the similarity in dimensions.

UTS, UCS and USS,—Ultimate tensile, compressive and shear strength, respectively
NA—not available
[i]human wet femoral compact bone (age span 10 to 79 years) from: Yamada, H. In: *Strength of biological materials*. Williams & Wilkins Co, Baltimore. pg 20 (1970).
[ii]age span 19 to 80 years; Reilly et al., "The elastic and ultimate properties of compact bone tissue" *J Biomech* 8: 393-405 (1975).
[iii]Carter et al., "Mechanical properties and composition of cortical bone" *Clin Orthop & Related Res* 135: 192-217 (1978).
[iv]An, Y H., "Mechanical properties of bone" In: *Mechanical testing of bone and the bone implant interface* An & Draughn, Eds. CRC Press, New York (2000).
[v]wet long bones, average for femur and humerus from: Yamada, H. In: *Strength of biological materials*. Williams & Wilkins Co, Baltimore. pg 54 (1970).
[vi]Silbernagel et al., "Validation of canine cancellous and cortical polyurethane foam bone models" *Vet Comp Orthop Traumatol* 15: 200-204 (2002).
[vii]matweb.com To mimic a gap fracture model, the synthetic bone specimens were manufactured in two symmetrical halves. Each half of the bone model features a linking segment 39 used for attachment to the holding fixtures 40, a tapering segment 41 representing the metaphyseal region and final segment 42 representing the diaphysis. This particular embodiment shows an ILNn locking mechanism comprising two SCPs 36 in combination with two plugs 25. (FIG. 12). The wall thickness was 2.5 mm throughout. Overall, the length of the tibial model, between each holding fixture, including a 50 mm central gap, was consistently 210 mm.

Figure 13:
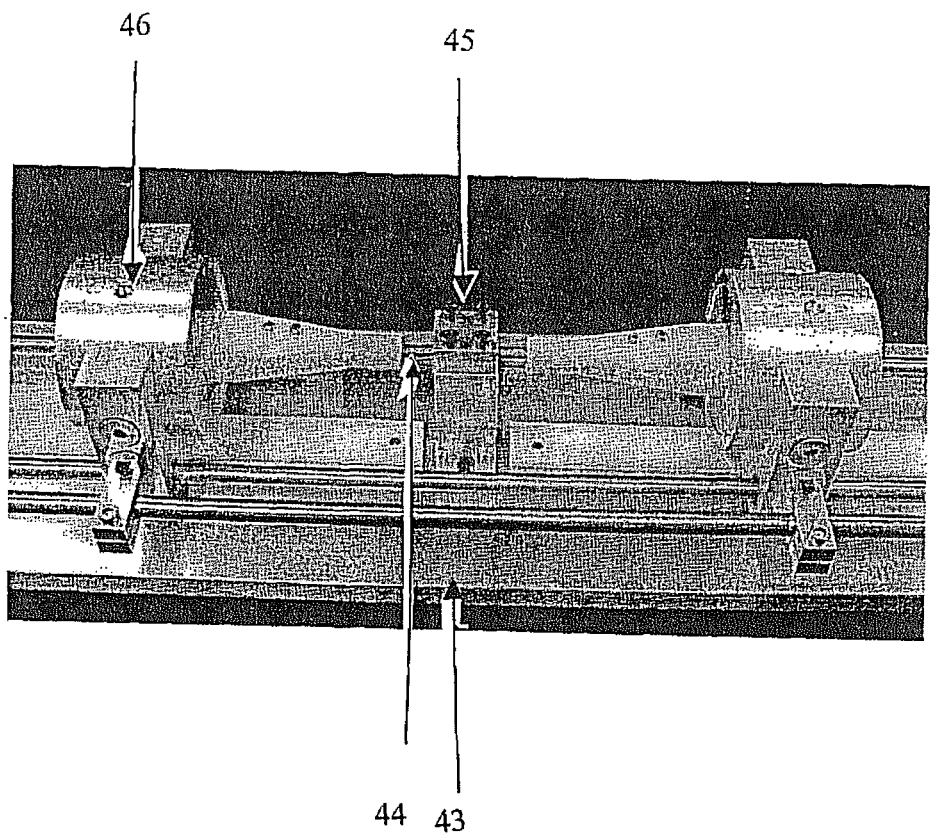
FIG. 13 shows one embodiment of an alignment fixture designed to ensure consistent positioning of ILNn's in all planes. It can be seen that the long axis of each nail is co-axial with a torsion fixture and all ILNns are centered between the loading cups.

To allow accurate and consistent placement of the bone screws or SCPs, a custom designed drilling fixture was used to pre-drill pilot holes in all bone models. The OD of the pilot holes was 2.5 mm for the ILN8, and 4 mm (cis-cortex) and 3.2 mm (trans-cortex) for the ILNn & SCP. This standardized procedure allowed all nails to be precisely and reliably centered longitudinally within the bone model. A matching alignment fixture 43 was used during implantation to ensure that all of the nails were also axially aligned within the bone models. FIG. 13 shows one embodiment of an alignment fixture designed to ensure consistent positioning of ILNn's in all planes. It can be seen that the long axis of each ILN 44 is co-axial with a torsion fixture 45 and all ILNns are centered between the loading cups 46.

Custom-made polyurethane foam plugs were inserted at the extremities of the bone model in order to maintain the ILNs in a centralized position during testing.

Study design—The ILN8's, SCP's, and ILNn's were tested using the synthetic tibial model in 2 groups using a total of 4 specimens per group as follows: i) ILN8 group: 8×185 mm conventional ILN with four bicortical 3.5 mm bone screws; ii) ILNn group: 185 mm ILNn and a SCP. Sample sizes were determined using a power analysis (power>0.8) based on means and standard deviations obtained during a pilot study.

Mechanical testing—Specimens were tested non-destructively in torsion using a protocol described in a previous study. von Pfeil et al., "In vitro biomechanical comparison of plate-rod combination and interlocking nail constructs in a canine tibial gap fracture model" *Am J Vet Res* 66:1469-1656 (2005). All constructs were securely mounted in a torsion fixture custom-designed to ensure accurate axial alignment and consistent testing length in all specimens. The torsion fixture was linked to a servohydraulic testing machine (Instron) via a pinion assembly. Tests were run in load control with a torque level of ±5 Nm for 10 cycles.

Data acquisition—A 255 kg (2,500 N) load cell coupled with the hydraulic actuator recorded loads over time while actuator displacement (mm) was recorded simultaneously at a sampling rate of 250 Hz. Because constructs were tested under load control conditions, construct compliances (defined as the slope of the deformation versus load curve) were computed in the 10th cycle between ±1.5 Nm and ±5 Nm using linear regression ($r^2 > 0.99$). An et al., "Basic concepts of mechanical property measurements and bone biomechanics" An Y H, & Drauhgn R A, eds. In: *Mechanical testing of bone and the bone implant interface*. New York: CRC Press, pp. 23-39 (2000). Total construct compliance, calculated as the average between compliances during positive and negative loading, was used for statistical analysis.

Figure 14:
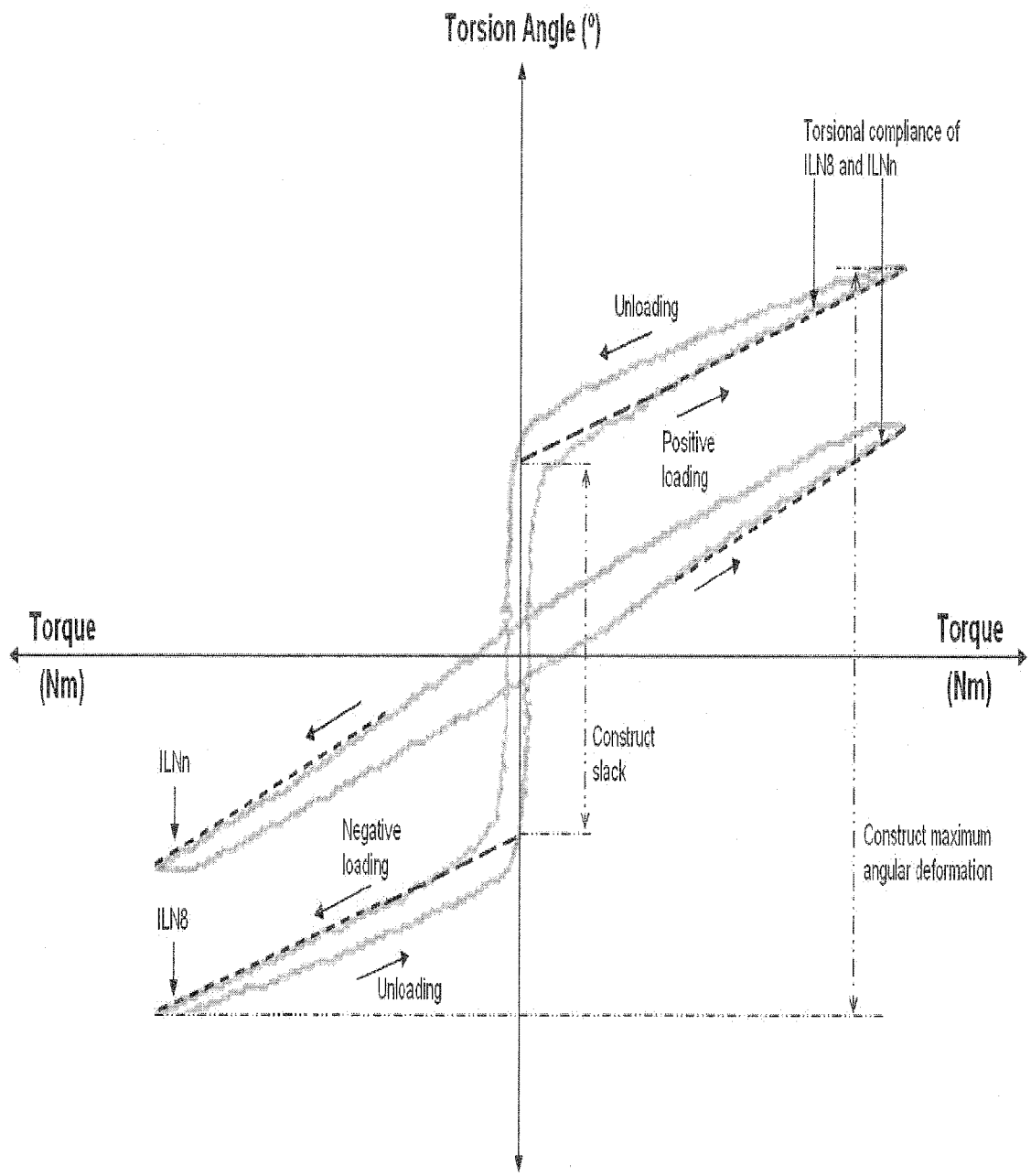
FIG. 14 shows exemplary data of torsion curves for the ILN8 and ILNn. The ILN8 displays a bimodal shape while the ILNn displays a unimodal shape. Compliance values were computed as the change in torsion angle from 1.5 Nm to ±5 Nm in the positive and negative loading phases. For the ILN8, bimodal curve construct slack was calculated as the difference between the y-intercept of the positive and negative compliances. Construct maximum angle deformation was calculated as the difference in torsion angle between the maximum and minimum applied torque.

Construct angular deformation was computed from actuator displacement data and the geometrical dimensions of the torsion fixture. Construct slack was documented when the compliance curves appeared bimodal and was computed as the difference between the y-axis intercept of the compliance slopes on the positive and negative loading curves (FIG. 14).

Data Analysis—The computed AMIs of the SCP, ILNn, and ILN8 were qualitatively compared to those of ILN8 and br-DCP as reported in the literature. Muir et al., "Area moment of inertia for comparison of implant cross-sectional geometry and bending stiffness" *Vet Comp Orthop Traumatol* 8:146-152 (1995); and Hulse et al., "Reduction in plate strain by addition of an intramedullary pin" *Vet Surg* 26:451-459 (1997). Construct compliance and angular deformation data were each compared using one-factor ANOVA. Student-Newman-Keuls post-hoc tests were used whenever significant differences were identified. The significance level was set at $p < 0.05$.

Results

Area moment of inertia—The AMI of the 3.5 mm, 4.5 mm screw, 3.5 mm bolt and SCP are reported in Table 5.

TABLE 5

Comparative area moment of inertia of standard bone screws, bolt and various sections of the novel SCP locking device. Area moment of inertia (mm$^4$)

| | |
|---|---|
| 3.5 mm screw | 1.63 |
| 4.5 mm screw | 3.98 |
| 3.5 mm bolt | 7.36 |
| Screw-Cone-Peg (SCP) | |
| Threaded section (core 4 mm) | 12.57 |
| Mid-tapered section (core 3.6 mm) | 8.24 |
| Smooth solid section (core 3.2 mm) | 5.15 |

The AMI of the various sections of the SCP were always larger than those of 3.5 mm or 4.5 mm screws (core diameter 2.4 mm and 3.0 mm, respectively). In addition, the SCP threaded section had a greater AMI than a 3.5 mm bolt. Nail AMIs are reported in Table 6.

TABLE 6

Comparative area moment of inertia of various sections of standard interlocking nails (conventional ILN), 3.5 mm broad dynamic compression plate (br-DCP) and of the novel hourglass-shaped nail (ILNn)

| | Area moment of inertia (mm$^4$): | | | |
|---|---|---|---|---|
| | ILN8 (3.5) | ILNn | ILN8 (4.5) | 3.5 broad DCP |
| Central section (solid) Nail hole level | 201.06 | 63.62 | 201.06 | ~55[23], ~59* |
| Mediolateral bending | 65.6 | 62.1 | 37.94 | ~32* |
| Craniocaudal bending | 174.18 | 171.43 | 146.45 | ~500* |

*based on a ~3.9 × 11.95 mm (plate cross section) and a ~5.55 × 3.9 mm (hole cross section), and assuming rectangular cross sections for both plate and screw hole.
Note that the AMIs of the ILN8 with 3.5 mm screws and ILNn are similar in both bending directions. Conversely, the AMI of the ILN8 with 4.5 screws (a nail prone to failure at the level of the nail hole) is considerably smaller than that of the ILNn, particularly in mediolateral bending.

The ILNn AMI at the nail holes were similar to those of an ILN8 with 3.5 mm screws and larger than those of the ILN8 with 4.5 mm screws in both the mediolateral and craniocaudal planes. Finally, the ILNn central section had an AMI greater than that of a 3.5 mm br-DCP. Muir et al., "Area moment of inertia for comparison of implant cross-sectional geometry and bending stiffness" *Vet Comp Orthop Traumatol* 8:146-152 (1995).

Construct compliance—Compliance curves for the ILN8 were bimodal, whereas compliance curves for the ILNn were unimodal. FIG. 14. In the bimodal graphs of the ILN8 there is no quantifiable torque in the central region, which corresponds to the change in the direction of torque. For all practical purposes this region represented the slack in the construct and reflected an abrupt change in angular deformation without resistance to applied torques. Conversely, due to the unimodal shape of the ILNn compliance curves, there was no region of slack in the ILNn specimens. The ILN8 construct was significantly less compliant ($p < 0.001$) at $821 \pm 7 \, 10^{-3}$°/Nm (mean±SD) than the ILNn construct at $1022 \pm 11 \, 10^{-3}$°/Nm (mean±SD).

Construct angular deformation—Maximum angular deformation of the ILN8 construct was significantly greater (p<0.001) than that of the ILNn construct (23.12±0.65° and 9.45±0.22°; mean±SD, respectively). Construct slack in the ILN8 group was 15.15±0.63°. Angular deformation for the ILN8 construct, once slack was overcome (at high torques), was significantly less (p<0.001) than that of the ILNn construct (7.97±0.05° and 9.45±0.22°, respectively).

Example IV

Hour-Glass ILNn Insertion Into A Raptor

A raptor (approximately 5 kg and 14 years old) will be initially examined and radiography will reveal a mildly dehydrated bird (<5%), in good flesh (as assessed by pectoral muscle palpation), with a open, grade II transverse, midshaft, Winquist-Hansen type II comminuted left tibiotarsal fracture and associated soft tissue trauma. The distal portion of the fibula will also sustained a comminuted fracture.

Initial treatment involves fluid therapy (70 ml of warm 0.9% NaCl s.c.), analgesia with butorphanol tartrate (Torbugesic®, Fort Dodge Animal Health, Overland Park, Kans. 66225, USA; 1 mg/kg q.i.d. 4 d), and antimicrobial therapy with enrofloxacin, (Baytril®, Bayer Corporation, Shawnee Mission, Kans., 66201, USA; 20 mg/kg, i.m.) then continued p.o. s.i.d. 10 d mixed 50:50 with lactated ringers solution. Treatment also involves force feeding with four furred, weanling rats injected with 10 ml of lactated ringers solution, application of a Robert Jones bandage to the affected limb and confinement in a 1.27 m×2.03 m×2.54 m, quiet, isolated cage.

Three days after admission the bird will be physically restrained for preanesthetic medication with a combination of butorphanol tartate (0.5 mg/kg) i.m. and midazolam (Midazolam Hydrochloride Injection, Abbot Laboratories, North Chicago, Ill. 60064, USA; 0.5 mg/kg, i.m). Five minutes later, anesthesia will be induced via face mask with 5% isoflourane in 2 L oxygen and subsequently intubated with a 6.5 mm uncuffed endotracheal tube. The bird is maintained on 2-3.5% isoflourane and a 22 g i.v. catheter placed in the brachialis vein through which 50 ml of lactated ringers solution was administered over 1 hr. Preoperative radiographs will be made and the surgery site cleaned, debrided and thoroughly plucked of feathers. The bird will recover 75 min after onset of anesthesia. Eighteen hours later the same anesthetic protocol will be repeated and surgery performed.

Closed reduction of the fracture will be accomplished. A normograde approach places an approximate 112 mm length, four hole hourglass shaped ILNn into the tibia. The ILNn will be inserted under fluoroscopic guidance with the stifle joint in 90° flexion. A medial parapatellar approach caudomedial to the enemial crest on the medial aspect of the tibial plateau is employed. A tibial extension piece is secured to the proximal end of the conventional ILN and a drill guide jig will be attached to the extension piece allowing accurate placement of transcortical screws through holes in the conventional ILN. The conventional ILN is seated approximately 6 mm into the tibia as judged by 2 mm marking intervals on the extension set. SCPs are placed through the most proximal and the most distal holes of the ILNn. Postoperative radiographs will revealed satisfactory placement of the screws and proper limb alignment.

Surgery time will be approximately 60 min and with a total time under anesthesia approximately between 100 to 110 min. A Robert Jones bandage is applied to the affected leg along with a tail guard. Recovery is expected to be uneventful. Six hours after recovery from anesthesia the Robert Jones bandage will be physically removed and replaced by a non-adherent wound dressing (Telfa®, Kendall Company, Mansfield, Mass. 02048, USA) covered by a thin gauze bandage and bandaging tape (Vetrap®, 3M Animal Care Products, St Paul, Minn. 55144, USA) that remains in place for 1 week. Supportive therapy during rehabilitation includes analgesia and antimicrobial therapy as well as calcium 250 mg and vitamin D (as cholicalciferol) 125 I.U. (Oyst-Cal-D, Goldline Laboratories, Miami, Fla. 33137, USA) p.o. s.i.d. for 20 days and oral vitamin B supplementation (Nutri-Cal, Tomlyn Products, Buena, N.J. 08310, USA) p.o. s.i.d. for 3 days. Supplements are given as a precautionary measure although there should not be any evidence of nutritional deficiency. Diet is as previously described except force feeding will no longer be necessary and eight weanling rats will be supplied daily (half filled with fluids).

On visual examination 48 hr postoperatively, the bird should be bearing weight on both limbs. Radiographs are made at 4 weeks and 11 weeks postoperatively. At 4 weeks, callus formation with osteosynthesis should occur incorporating most fibular and tibiotarsal fragments into the callus. Radiographic union (bridging callus over 3 of 4 cortices) is expected by 4 weeks postoperatively. There is no observable SCP bending or apparent torsional strain on the ILNn.

At 5 weeks, the bird will be moved to a larger enclosure, as callus for should be sufficient to withstand the bird's increased activity level. At 11 weeks, there a radiographic union of the main fragments and incorporation of most of the remaining fragments into a single solid callus is apparent. At 12 weeks postoperatively, the bird is sent for rehabilitation to a licensed facility with a 30.5 m×6.1 m×4.9 m flight cage. The bird should again weigh approximately 5 kg at this time. No physical, behavioral or other assessable impairment, that would preclude release, is found during the rehabilitation period and the bird is released 5 mo post admission.

Example V

Comparison of ILNn and Conventional ILN Using Mongrel Dogs

This example will determine and compare the short-term biological outcome of one embodiment of an ILNn system to two different conventional ILN designs and a DCP for several post-operative and post-mortem parameters such as orthopaedic examination, plain and high resolution radiography, force plate gait analysis, histology, and biomechanical testing.

Detailed Methodology

Implants: Standard 6 mm ILNs (length 185 mm with 2 proximal and 2 distal screw holes), as well as 2.7 mm screws and bolts will be obtained from Innovative Animal Products, Rochester, Minn. The novel ILNs and screws will be manufactured and provided by BioMedtrix, Boonton, N.J. A 12-hole 3.5 mm DCP and 3.5 mm screws will be obtained from Synthes, Paoli, Pa.

Animals: Eighteen dogs will be obtained from a commercial vendor (R&R) approved by ULAR. To reduce variability between dogs, all dogs will be selected based on tibial size (210 mm:length by 8 mm:medullary diameter), which will be confirmed radiographically. Dogs must be free from any systemic and orthopaedic diseases based on physical/orthopaedic examination, complete blood count, blood chemistry, and urinalysis. Degenerative joint disease (DJD) will be ruled out based on stifle and hip radiographs under sedation. The dogs will be housed in the vivarium of the College of Veterinary Medicine (CVM) at MSU. All dogs will be trained to walk on the force plate track once daily pre-operatively to establish baseline values of PVGRF and AVI.

Experimental Groups: Dogs will be randomly divided into 4 groups. Two groups will be tested using either screws or bolts in conventional ILN6's (n=5, each group). A third group will be tested using an ILNn system (n=5). The fourth group will be tested using a dynamic compression plate (DCP) (n=3). Specifically:

Group 1: 6 mm×185 mm conventional ILN with 4 bicortical 2.7 mm screws—(ILN6s)
Group 2: 6 mm×185 mm conventional ILN with 4 bicortical 2.7 mm bolts—(ILN6b)
Group 3: ILNn with 4 bicortical screws
Group 4: 12-hole 3.5 mm DCP with 12 cortical 3.5 mm screws Surgical Procedures: The surgical procedure will be similar to a previous study. Klein et al., "Comparison of unreamed nailing and external fixation of tibia diastases-mechanical conditions during healing and biological outcome" *J Orthop Res* 22:1072-1078 (2004).

Pre-operative Phase: The dogs will be fasted, premedicated, and anesthetized following standard procedures. In particular, all dogs will receive an epidural of morphine in addition to gas anesthesia. Antibiotics will be given pen-operatively (IV) and 3 days post-operatively (oral).

Nail implantation and ostectomy: (n=5/group): The animal will be placed in dorsal recumbency and the left hind limb will be draped according to routine aseptic techniques. Exposure will be based on the principle of minimally invasive surgical techniques. This approach will allow preservation of the soft tissue and blood supply surrounding the fracture. A left medial parapatellar arthrotomy will be made and gentle retraction of the patellar fat pad will be conducted to identify the nail insertion point (cranial to the tibial insertion of the cranial cruciate ligament). With the knee in 90° of flexion, a small-diameter (⅛th in) Steinmann pin will be inserted in a normograde fashion to ensure the correct alignment with the tibial medullary cavity. The pin will be removed followed by insertion of the nail. The nail will be temporarily stabilized with locking devices placed via small medial skin incisions over the proximal and distal tibial metaphyses. Next, the nail will be pulled back past the mid-shaft. A 2 cm skin incision will be made at the cranio-lateral aspect of the mid-diaphysis. The underlying musculature will be retracted laterally to reveal the tibia and fibula. A 5 mm transverse mid-shaft ostectomy of the tibia and fibula will be performed using a bone saw and a custom made fixture to guarantee accuracy of the gap width between specimens. The nail will then be inserted in a normograde fashion past the mid-shaft ostectomy until it is securely seated. Next, screws or bolts will be re-inserted for final fixation through the previously drilled holes. The entire procedure will be conducted with fluoroscopy guidance to ensure proper placement of pins, nails, and locking devices. Routine closure of all surgical wounds in layers will conclude the surgical procedure.

Bone plate (DCP) implantation and ostectomy (n=3): A standard medial approach to the tibia will be used. The underlying fascia will be retracted to reveal the tibial diaphysis. An anatomically contoured 3.5 mm 12-hole DCP will be applied to the medial surface of the tibia, then temporarily stabilized with two 3.5 mm screws both distally and proximally. The purpose of the temporary fixation is to ensure anatomical alignment following ostectomy. The bone plate will be removed and the tibio-ulnar ostectomy will be performed, as described above. Final plate fixation will be achieved with 6 bone screws on each side of the ostectomy. Routine closure in layers will conclude the surgical procedure.

Post-operative procedures: Dogs will be recovered in the vivarium following standard procedures. In particular, the dogs will be given one dose of analgesics (buprenorphine 0.01 mg/kg IM) immediately post-surgery then as needed following surgery. The operated limb will be checked daily for signs of swelling, erythema, and dehiscence until complete healing. A routine physical examination will be performed daily throughout the course of the study and the observations recorded.

Post-Operative Evaluation and Data Collection

Orthopaedic examination (objective data): Each dog will be evaluated for lameness associated with the operated limb prior to each force plate evaluation. A numerical lameness/weight-bearing/pain scoring system will be used. Tibial torsional stability will be assessed subjectively under sedation prior to radiography. The orthopaedic examination will be conducted once every other week.

Radiographic examination (descriptive data): Two standard orthogonal radiographic views of the implanted tibiae will be taken under sedation before and after surgery then every two weeks until study completion. Radiographic assessment of gap fracture healing, will be qualitatively evaluated over time by a board certified orthopaedic surgeon. Radiographs will be used to determine the end point of the study. The study will be concluded when clinical union is achieved in at least one group. Clinical union is defined as bridging of 3 out of 4 cortices on two orthogonal radiographic views.

Force plate analysis (objective data PVGRF and AVI): Force plate analysis will be conducted according to established protocols. DeCamp et al., "Kinematic gait analysis of the trot in healthy greyhounds" *Am J Vet Res* 54:627-634 (1993). For each hind limb, data from the first 4 valid trials (velocity 1.70-2.20 m/s, acceleration+0.8 m/s2) will be used. Gait analysis will be performed prior to surgery (baseline values) then every other week until study completion. To optimize data collection, the dogs will be trained to walk along the force plate walkway prior to surgery and three times a week during the study.

High Resolution Contact Radiography (HRCR—quantitative data): At the conclusion of the study, all animals will be humanely euthanized with a bolus injection of sodium pentobarbital. Both tibiae of each dog will be harvested and the implants will be extracted from the operated specimens. During dissection and explantation, care will be taken to preserve the callus and surrounding soft tissue for subsequent histological analysis. The mid diaphysis of the operated tibiae will undergo HRCR to obtain high-detailed images of the bony callus. HRCRs will be digitized and the cortical, periosteal and endosteal callus areas will be measured using NIH Image software.

Biomechanical testing (torsional stiffness and torque to failure—objective data): Immediately following the HRCR, specimens will be wrapped in saline-soaked towels, stored in two zip-lock-plastic bags, and frozen at −80° C. until biomechanical testing. Twenty-four hours prior to testing, specimens will be thawed overnight in a 4° C. refrigerator. Specimens will be kept moist throughout the entire testing period by spraying isotonic saline. Specimens will be embedded in epoxy using a custom-designed potting fixture. The fixture will be modified to ensure axial alignment of the tibiae and torsional fixture. Tibial specimens (intact and experimental contralateral) will be loaded in torsion non-destructively initially, then until failure. Pure torsional loading will be achieved using a pinion assembly system that converts linear displacement of the servo-hydraulic actuator into rotation of the proximal cup of the torsion fixture, while the distal cup remains fixed. Angular deformation will be computed based on the geometry of the pinion assembly. A 2000 N load cell coupled with the hydraulic actuator will record loads over time, while actuator displacement will be recorded simultaneously at a sampling rate of 250 Hz. The loading fixtures will be instrumented with rotary encoders to further document angular deformation of the constructs and with a 200 Nm torque load cell to further document the magnitude of the applied torques.

Non-destructive tests will be run for ten cycles using a sinusoidal waveform (0.1.25 Hz) with a torque level set at 10% of the mean torque to failure of intact tibiae of similar sizes. Data (i.e., for example, load, actuator displacement, torque, and angular deformation) will be taken at the 10th cycle. Torsional stiffness)(Nm/°) will be defined as slope of load/torque over deformation/angle of twist curves.

Following non-destructive tests, specimens will be loaded to failure at a ramp rate of 60°/second. In the experimental specimens, a dedicated software routine will be used to allow immediate interruption of the test once an abrupt drop in load is detected. This load drop will be defined as a sharp (>10%) decrease in applied load. This feature will reduce damage to the callus, allowing minimal artifact during subsequent histological evaluation of the specimen. The torque-to-failure will be recorded as the torque immediately prior to the abrupt drop in applied load. Mean torsional stiffness and mean failure torque will be reported as a percentage of those of the contralateral tibiae.

Histology (quantitative and descriptive data): Following the biomechanical testing, operated specimens will be "reassembled" and preserved in 10% buffered formalin for histological analysis. The same tibia (callus region) tested biomechanically will be used for histological analysis to: 1) decrease the number of animals used in the study while optimizing data collection; and 2) allow direct correlation between biomechanical and histological data on the same specimen. Fixed specimens will be processed for histological analysis. Specifically, the specimens will be trimmed as needed and the mid diaphysis, including at least 2 cm on either side of the ostectomy site, will be decalcified in buffered formic acid. Specimens will then be embedded in paraffin blocks and sectioned using standard histological methods. Every 5th slide will be stained with hematoxylin and eosin (H&E) while the remaining slides will be kept for additional staining if needed. Each section will be analyzed using a Bioquant™ TCW-98 image analysis system for quantitative histomorphometry. The sections will be divided into 3 compartments (cortical, periosteal and endosteal) and volume fractions of native bone, new bone ingrowth and soft tissue in each compartment will be determined. Type of bone formation (woven and lamellar) will be evaluated under polarized light and described. A pathology narrative will be provided along with tabulated pathology data and representative digital images.

Statistical Analysis: Lameness scores and gait analysis data (PVGRF and AVI) will be compared using repeated measures ANOVA. Biomechanical data (torsional stiffness and torque to failure) will be compared using 2-factor (limb {i.e., the repeated factor} and implant) repeated measures ANOVA. Data from HRCR and histology will be compared using 1-factor ANOVA. Student-Newman-Keels post-hoc tests will be used whenever significant differences are identified ($p<0.05$).

It is believed that the data will show that deleterious torsional and shear forces are counteracted by the ILNn implant fixation technique. The data will verify recent clinical and experimental reports in the both human and veterinary literature showing that currently available ILNs do not provide sufficient post-operative torsional stability as initially expected. Further, the ILNn system will eliminate undesirable instability associated with the traditional conventional ILN system. Also, the in vitro mechanical data will demonstrate a significantly improved torsional stability of the ILNn design.

The embodiments of the invention above have been disclosed for the purpose of illustration and should not be construed to limit the breadth of the following claims. Variations and modifications of the disclosed embodiments, which fall within the concepts of this invention, will be readily apparent to persons skilled in the art. All such variations and modifications are intended to be encompassed by the claims set forth below.

I claim:

1. A method for providing support for a fractured bone, comprising:
   a) providing:
      i) a bone comprising a cortex and an inner volume within the cortex;
      ii) an intramedullary nail, comprising a first end section, a central section and second end section, wherein each have a diameter, and wherein at least one of the end sections has at least one substantially transverse conical hole therethrough, wherein the transverse conical hole has an inner surface, and wherein the diameter of the first and second end sections are larger than the diameter of the central section; and
      iii) one or more screws each comprising a cylindrical first end section, a conical central section, and a cylindrical second end section with threads; wherein the conical central section of the screw has an outer surface configured to fit with the transverse conical hole inner surface;
   b) placing at least a portion of the intramedullary nail into the inner volume of the bone; and
   c) inserting the screw into the transverse conical hole such that the screw conical central section outer surface contacts the conical hole inner surface and the cylindrical first end section of the screw protrudes from the nail and contacts the bone cortex, the conical central section of the screw contacts the nail, and the cylindrical second end section of the screw protrudes from the nail and threads into the bone cortex.

2. The methods of claim 1, wherein inserting the screw into the transverse conical hole further comprises tightening the screw in the transverse conical hole.

3. The method of claim 1, wherein the screw conical central section further comprises threads and the conical hole further comprises threads, and wherein inserting the screw into the transverse conical hole further comprises tightening the screw in the transverse conical hole so that the screw conical section threads and the transverse conical hole threads interlock.

4. The method of claim 1, wherein the method is practiced during a surgical procedure on a human.

5. The method of claim 1, wherein the method is practiced during a surgical procedure on an animal which is not human.

6. A method for providing support for a fractured bone, comprising:
   a) providing:
      i) a subject with a fractured bone, said fractured bone comprising a cortex and an inner volume:
      ii) an intramedullary nail, comprising a first end section, a central section and second end section, wherein each have a diameter and wherein at least one of the end sections has at least one substantially transverse conical hole therethrough, wherein the transverse conical hole has an inner surface, and wherein the diameter of the first and second end sections are larger than the diameters of the central section; and iii) one or more screws each comprising a cylindrical first end section, a conical central section, and a cylindrical second end section with threads; wherein the conical central section of the screw has an outer surface configured to fit with the transverse conical hole inner surface;

b) placing at least a portion of the intramedullary nail into the inner volume of the bone;

c) drilling one or more holes through the bone col iex in a location which is substantially in line with a transverse conical hole in the nail; and d) inserting the screw into the hole in the bone cortex and transverse conical hole such that the screw conical central section outer surface contacts the conical hole inner surface, the cylindrical first end section of the screw protrudes from the nail and contacts the bone cortex, the conical central section of the screw contacts the nail, and the cylindrical second end section of the screw protrudes from the nail and threads into the bone cortex.

7. The method of claim 6, wherein the subject is human.

8. The method of claim 6, wherein the subject is not human.

9. The method of claim 6, further comprising removing the screw and nail from the bone after the fracture heals.

\* \* \* \* \*